US012322497B2

(12) United States Patent
Heldt et al.

(10) Patent No.: US 12,322,497 B2
(45) Date of Patent: Jun. 3, 2025

(54) EMBOLI DETECTION METHODS TO IDENTIFY MECHANISMS OF BRAIN INJURY IN SUSCEPTIBLE ADULTS AND CHILDREN

(71) Applicants: Massachusetts Institute of Technology, Cambridge, MA (US); Children's Medical Center Corporation, Boston, MA (US)

(72) Inventors: Thomas Heldt, Cambridge, MA (US); Syed Muhammad Imaduddin, Cambridge, MA (US); Kerri Larovere, Andover, MA (US); Barry Kussman, Waban, MA (US)

(73) Assignees: Massachusetts Institute of Technology, Cambridge, MA (US); Children's Medical Center Corporation, Boston, MA (US)

(*) Notice: Subject to any disclaimer, the term of this patent is extended or adjusted under 35 U.S.C. 154(b) by 798 days.

(21) Appl. No.: 17/601,603

(22) PCT Filed: Apr. 8, 2020

(86) PCT No.: PCT/US2020/027249
§ 371 (c)(1),
(2) Date: Oct. 5, 2021

(87) PCT Pub. No.: WO2020/210344
PCT Pub. Date: Oct. 15, 2020

(65) Prior Publication Data
US 2022/0181008 A1 Jun. 9, 2022

Related U.S. Application Data

(60) Provisional application No. 62/831,678, filed on Apr. 9, 2019.

(51) Int. Cl.
*G16H 30/40* (2018.01)
*A61B 8/00* (2006.01)
(Continued)

(52) U.S. Cl.
CPC .............. *G16H 30/40* (2018.01); *A61B 8/06* (2013.01); *A61B 8/0808* (2013.01);
(Continued)

(58) Field of Classification Search
CPC ..... A61B 8/0808; A61B 8/0891; A61B 8/488; A61B 8/06; A61B 8/448; G01S 15/8979
See application file for complete search history.

(56) References Cited

U.S. PATENT DOCUMENTS 5,103,827 A 4/1992 Smith
5,348,015 A * 9/1994 Moehring ........... G01S 7/52038
600/453

(Continued)

OTHER PUBLICATIONS

N. Aydin et al, "Embolic Doppler Ultrasound Signal Detection Using Discrete Wavelet Transform", IEEE Transactions on Information Technology in Biomedicine, vol. 8, No. 2, pp. 182-190, Jun. 2004 (Year: 2004).*

(Continued)

*Primary Examiner* — Joel Lamprecht
*Assistant Examiner* — Nyrobi Celestine
(74) *Attorney, Agent, or Firm* — Wolf, Greenfield & Sacks, P.C.

(57) ABSTRACT

Techniques for detecting embolic information for a patient. The techniques may include obtaining data identifying an ultrasound signal associated with the patient, identifying a set of candidate embolic regions in the data, identifying a set of embolic regions from among the set of candidate embolic regions, and outputting embolic information corresponding to the set of embolic regions.

20 Claims, 16 Drawing Sheets

(51) Int. Cl.

| | |
|---|---|
| *A61B 8/06* | (2006.01) |
| *A61B 8/08* | (2006.01) |
| *G01S 7/52* | (2006.01) |
| *G01S 15/89* | (2006.01) |
| *G16H 50/20* | (2018.01) |
| *G16H 50/30* | (2018.01) |

(52) U.S. Cl.
CPC ............ *A61B 8/0891* (2013.01); *A61B 8/488* (2013.01); *G01S 7/52036* (2013.01); *G01S 15/8952* (2013.01); *G01S 15/8979* (2013.01); *G16H 50/20* (2018.01); *G16H 50/30* (2018.01)

(56) References Cited

U.S. PATENT DOCUMENTS

| | | | | |
|---|---|---|---|---|
| 5,441,051 | A * | 8/1995 | Hileman | A61B 8/06 600/454 |
| 6,616,611 | B1 * | 9/2003 | Moehring | G01S 15/8988 600/441 |
| 2005/0075568 | A1 | 4/2005 | Moehring | |
| 2005/0251041 | A1 * | 11/2005 | Moehring | A61B 8/488 600/455 |
| 2006/0264759 | A1 * | 11/2006 | Moehring | A61B 8/06 600/469 |
| 2014/0194740 | A1 * | 7/2014 | Stein | A61B 8/565 600/455 |
| 2017/0004619 | A1 | 1/2017 | Liang et al. | |
| 2020/0237315 | A1 * | 7/2020 | Mazar | A61B 5/7225 |

OTHER PUBLICATIONS

D. Xu et al, "An automated feature extraction and emboli detection system based on the PCA and fuzzy sets", Computers in Biology and Medicine, vol. 37, pp. 861-871, 2007 (Year: 2007).*
H. Nakamura et al, "Detection of Venous Emboli Using Doppler Ultrasound", European Journal of Vascular and Endovascular Surgery, vol. 35, No. 1, pp. 96-101, Jan. 2008 (Year: 2008).*
C. Banahan et al, "Sizing Gaseous Emboli Using Doppler Embolic Signal Intensity", Ultrasound in Medicine and Biology, vol. 38, No. 5, pp. 824-833, 2012 (Year: 2012).*
B. Silbert et al, "Review of Transcranial Doppler Ultrasound to Detect Microemboli during Orthopedic Surgery", American Journal of Neuroradiology, vol. 35, No. 10, pp. 1858-1863, Oct. 2014 (Year: 2014).*
M. Geryes et al, "Detection of Doppler Microembolic Signals Using High Order Statistics", Computational and Mathematical Methods in Medicine, vol. 2016, No. 3243290, pp. 1-8, Nov. 2016 (Year: 2016).*
S. Menigot et al, "Automatic detection of microemboli by means of a synchronous linear prediction technique", 2009 IEEE International Ultrasonics Symposium (IUS), pp. 20-23, Sep. 2009 (Year: 2009).*
M. Geryes et al, "A New Energy Detector of Micro-Emboli Using a Time-Varying Threshold", 2015 International Conference on Advances in Biomedical Engineering (ICABME), pp. 89-92, 2015 (Year: 2015).*
M. Geryes, "Development of signal processing algorithms for the detection of micro-emboli using a new TCD system", Signal and Image Processing, pp. 1-129, Jan. 2017 (Year: 2017).*
B. Guepie et al, "Sequential Emboli Detection From Ultrasound Outpatient Data", IEEE Journal of Biomedical and Health Informatics, vol. 23, No. 1, pp. 334-341, Jan. 2019 (Year: 2019).*
M. Geryes et al, "Enhanced weak Doppler micro-embolic signal detection using energy fluctuations", Biomedical Signal Processing and Control, vol. 47, pp. 177-182, Aug. 2018 (Year: 2018).*
International Search Report and Written Opinion for International Application No. PCT/US2020/027249 mailed Sep. 14, 2020.
International Preliminary Report on Patentability for International Application No. PCT/US2020/027249 mailed Oct. 21, 2021.

Aydin et al., The use of the wavelet transform to describe embolic signals. Ultrasound in medicine & biology. Jul. 1, 1999;25(6):953-8.
Banahan et al., An in vitro comparison of embolus differentiation techniques for clinically significant macroemboli: dual-frequency technique versus frequency modulation method. Ultrasound in medicine & biology. Nov. 1, 2014;40(11):2642-54.
Barbaro et al., Pediatric extracorporeal life support organization registry international report 2016. ASAIO journal (American Society for Artificial Internal Organs: 1992). Jul. 2017;63(4):456-63.
Bovik et al., A generalization of median filtering using linear combinations of order statistics. IEEE Transactions on Acoustics, Speech, and Signal Processing. Dec. 1983;31(6):1342-50.
Brucher et al., Automatic online embolus detection and artifact rejection with the first multifrequency transcranial Doppler. Stroke. Aug. 1, 2002;33(8):1969-74.
Cohen, A coefficient of agreement for nominal scales. Educational and psychological measurement. Apr. 1960;20(1):37-46.
Colantonio et al., Microembolic signal characterization by transcranial Doppler imaging. Pattern Recognition and Image Analysis. Dec. 2007;17(4):567-77.
Darbellay et al., Solid or gaseous circulating brain emboli: are they separable by transcranial ultrasound?. Journal of cerebral blood flow & metabolism. Aug. 2004;24(8):860-8.
Eddins, The watershed transform: strategies for image segmentation. MatLab News & Notes. Math Works. Feb. 2002. 13 pages. https://www.mathworks.com/company/newsletters/articles/the-watershed-transform-strategies-for-image-segmentation.html [Last accessed Mar. 31, 2022].
Fan et al., Automated embolus identification using a rule-based expert system. Ultrasound in medicine & biology. Aug. 1, 2001;27(8):1065-77.
Geryes et al., A new energy detector of micro-emboli using a time-varying threshold. 2015 International Conference on Advances in Biomedical Engineering (ICABME). Sep. 16, 2015:89-92.
Girault et al., Synchronous detection of emboli by wavelet packet decomposition. 2007 IEEE International Conference on Acoustics, Speech and Signal Processing—ICASSP'07. Apr. 15, 2007:I-409.
Guépié et al., Sequential emboli detection from ultrasound outpatient data. IEEE Journal of Biomedical and Health Informatics. Feb. 21, 2018;23(1):334-41.
Imaduddin et al., Automated cerebral microembolus identification in pediatric patients using transcranial Doppler ultrasound. Abstract. American Institute of Ultrasound in Medicine Proceedings. Apr. 2019;38:111.
Imaduddin et al., A time-frequency approach for cerebral embolic load monitoring. IEEE Transactions on Biomedical Engineering. Jul. 10, 2019;67(4):1007-18.
Larovere et al., Cerebral High-Intensity Transient Signals during Pediatric Cardiac Catheterization: A Pilot Study Using Transcranial Doppler Ultrasonography. Journal of Neuroimaging. Jul. 2017;27(4):381-7.
Larovere et al., Patterns of head computed tomography abnormalities during pediatric extracorporeal membrane oxygenation and association with outcomes. Pediatric Neurology. Aug. 1, 2017;73:64-70.
Leunissen et al., Validation of the automated electronic microemboli detection system in patients undergoing carotid endarterectomy. Ultraschall in der Medizin—European Journal of Ultrasound. Apr. 2018;39(02):198-205.
Lipperts et al., Quantification of embolic showers using radio-frequency based TCD analysis. Ultrasound in medicine & biology. Mar. 1, 2009;35(3):395-402.
Lubbers et al., An ultrasonic detector for microgasemboli in a bloodflow line. Ultrasound in medicine & biology. Jan. 1, 1977;2(4):301-10.
Marinoni et al., Cerebral microemboli detected by transcranial doppler in patients treated with extracorporeal membrane oxygenation. Acta Anaesthesiologica Scandinavica. Aug. 2016;60(7):934-44.
Mchugh, Interrater reliability: the kappa statistic. Biochemia medica. Oct. 15, 2012;22(3):276-82.

(56) References Cited

OTHER PUBLICATIONS

Moehring et al., Power M-mode Doppler (PMD) for observing cerebral blood flow and tracking emboli. Ultrasound in medicine & biology. Jan. 1, 2002;28(1):49-57.

Moehring et al., Pulse Doppler ultrasound detection, characterization and size estimation of emboli in flowing blood. IEEE transactions on biomedical engineering. Jan. 1994;41(1):35-44.

Nasr et al., Neurologic complications of extracorporeal membrane oxygenation. Journal of Clinical Neurology. Oct. 1, 2015;11(4):383-9.

Otsu, A threshold selection method from gray-level histograms. IEEE transactions on systems, man, and cybernetics. Jan. 1979;9(1):62-6.

Reinhartz et al., Multicenter experience with the Thoratec ventricular assist device in children and adolescents. The Journal of heart and lung transplantation. Apr. 1, 2001;20(4):439-48.

Ringelstein et al., Consensus on microembolus detection by TCD. Stroke. Mar. 1998;29(3):725-9.

Riviere et al., Modeling and canceling tremor in human-machine interfaces. IEEE engineering in medicine and biology magazine. May 1996;15(3):29-36.

Rodriguez et al., Sources of variability in the detection of cerebral emboli with transcranial Doppler during cardiac surgery. Journal of Neuroimaging. Apr. 2006;16(2):126-32.

Russell et al., Online automatic discrimination between solid and gaseous cerebral microemboli with the first multifrequency transcranial Doppler. Stroke. Aug. 1, 2002;33(8):1975-80.

Seguchi et al., Evaluation of micro-emboli in a patient with ventricular assist device support with hemolysis. Journal of Artificial Organs. Sep. 2015;18(3):276-9.

Serbes et al., Analysis of embolic signals with directional dual tree rational dilation wavelet transform. 2016 38th Annual International Conference of the IEEE Engineering in Medicine and Biology Society (EMBC). Aug. 16, 2016:3821-24.

Smith et al., A comparison of four methods for distinguishing Doppler signals from gaseous and particulate emboli. Stroke. Jun. 1998;29(6):1133-8.

Zanatta et al., Microembolic signals and strategy to prevent gas embolism during extracorporeal membrane oxygenation. Journal of Cardiothoracic Surgery. Dec. 2010;5(1):1-5.

* cited by examiner

EMBOLI DETECTION METHODS TO IDENTIFY MECHANISMS OF BRAIN INJURY IN SUSCEPTIBLE ADULTS AND CHILDREN

RELATED APPLICATIONS

The present application is a national stage filing under 35 U.S.C. § 371 of International Patent Application No. PCT/US2020/027249, filed Apr. 8, 2020 and titled "EMBOLI DETECTION METHODS TO IDENTIFY MECHANISMS OF BRAIN INJURY IN SUSCEPTIBLE ADULTS AND CHILDREN," which claims the benefit under 35 U.S.C. § 119(e) to U.S. Application Ser. No. 62/831,678, filed Apr. 9, 2019 and titled "EMBOLI DETECTION METHODS TO IDENTIFY MECHANISMS OF BRAIN INJURY IN SUSCEPTIBLE ADULTS AND CHILDREN," each of which is incorporated herein by reference in its entirety.

FIELD

Aspects of the technology described herein relate to techniques for detecting emboli and embolic load using data obtained through ultrasound measurements on a patient or the patient's equipment.

BACKGROUND

Transcranial Doppler (TCD) ultrasound is a type of medical imaging that measures velocity of blood flow through the brain's blood vessels. A TCD device has an ultrasound probe that emits high-frequency sound waves (~2 MHz) and a sensor that detects echoes from the sound waves. The echoes can be analyzed to determine the characteristics of the blood flow. As a result of the Doppler effect, the frequencies of the echoes can be used to determine the direction and speed of the blood flow. For example, if the blood is moving away from the probe, then the frequency of the echo is lower than the emitted frequency. If the blood is moving towards the probe, then the frequency of the echo is higher than the emitted frequency. The echoes can be analyzed and converted into velocities to provide an image of blood flow within a blood vessel of a patient's brain. Another type of ultrasound imaging is pulsed mode ultrasound. In pulsed mode ultrasound, points on a received echo correspond to a depth in the imaging plane. If points from one depth are collected for successive pulse emissions, the frequency of the collected signal may be proportional to the velocity at that depth.

TCD ultrasound can detect emboli traveling in the brain, which can be a precursor for brain injury (e.g., stroke, delirium, and neurocognitive impairment). An embolus may be composed of gas or solid matter, and can cause partial or complete blockage of blood flow within a blood vessel in the brain, leading to stroke and other neurological complications. Examples of types of emboli include gas, thrombus (e.g., blood clot), atheromatous plaque, platelet-fibrin aggregates, and lipid (e.g., fat).

SUMMARY

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining data identifying an ultrasound signal associated with a patient; determining, using the data, a background signal representative of blood flow in the patient, the background signal oscillating over time; identifying at least one candidate embolic region in the data using the background signal; and outputting embolic information based on the at least one candidate embolic region.

Some embodiments are directed to at least one non-transitory computer-readable storage medium storing processor-executable instructions that, when executed by at least one hardware processor, cause the at least one hardware processor to perform: obtaining data identifying an ultrasound signal associated with a patient; determining, using the data, a background signal representative of blood flow in the patient, the background signal oscillating over time; identifying at least one candidate embolic region in the data using the background signal; and outputting embolic information based on the at least one candidate embolic region.

Some embodiments are directed to a method, comprising: obtaining data identifying an ultrasound signal associated with a patient; determining, using the data, a background signal representative of blood flow in the patient, the background signal oscillating over time; identifying at least one candidate embolic region in the data using the background signal; and outputting embolic information based on the at least one candidate embolic region.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining data identifying an ultrasound signal associated with a patient; identifying a plurality of embolic regions existing within a candidate embolic region of the data; and outputting embolic information corresponding to the plurality of embolic regions.

Some embodiments are directed to at least one non-transitory computer-readable storage medium storing processor-executable instructions that, when executed by at least one hardware processor, cause the at least one hardware processor to perform: obtaining data identifying an ultrasound signal associated with a patient; identifying a plurality of embolic regions existing within a candidate embolic region of the data; and outputting embolic information corresponding to the plurality of embolic regions.

Some embodiments are directed to a method, comprising: obtaining data identifying an ultrasound signal associated with a patient; identifying a plurality of embolic regions existing within a candidate embolic region of the data; and outputting embolic information corresponding to the plurality of embolic regions.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining data identifying an ultrasound signal associated with a patient, the data obtained by performing single frequency ultrasound measurements on a patient for a period of time; and identifying, during the period of time, embolic information for the patient based on the data.

Some embodiments are directed to at least one non-transitory computer-readable storage medium storing processor-executable instructions that, when executed by at least one hardware processor, cause the at least one hardware processor to perform: obtaining data identifying an ultrasound signal associated with a patient, the data obtained by performing single frequency ultrasound measurements on a patient for a period of time; and identifying, during the period of time, embolic information for the patient based on the data.

Some embodiments are directed to a method, comprising: obtaining data identifying an ultrasound signal associated with a patient, the data obtained by performing single frequency ultrasound measurements on a patient for a period of time; and identifying, during the period of time, embolic information for the patient based on the data.

Some embodiments are directed to a system comprising: at least one hardware processor; and at least one non-transitory computer-readable storage medium storing processor-executable instructions that, when executed by the at least one hardware processor, cause the at least one hardware processor to perform a method. The method comprises obtaining data identifying an ultrasound signal associated with a patient; identifying a set of candidate embolic regions in the data; and identifying a set of embolic regions from among the set of candidate embolic regions. Identifying the set of candidate embolic regions may comprise assigning a region in the data as being a candidate embolic region at least in part by using at least one statistical model relating at least one feature of the region to physiological information; and determining a plurality of candidate embolic regions associated with the region to include in the set of candidate embolic regions. Identifying the set of embolic regions from among the set of candidate embolic regions may comprise assigning at least one candidate embolic region of the set of candidate embolic regions as being an embolic region to include in the set of embolic regions, the assigning performed at least in part by using the at least one statistical model.

Some embodiments are directed to at least one non-transitory computer-readable storage medium storing processor-executable instructions that, when executed by at least one hardware processor, cause the at least one hardware processor to perform: obtaining data identifying an ultrasound signal associated with a patient; identifying a set of candidate embolic regions in the data; and identifying a set of embolic regions from among the set of candidate embolic regions. Identifying the set of candidate embolic regions may comprise assigning a region in the data as being a candidate embolic region at least in part by using at least one statistical model relating at least one feature of the region to physiological information; and determining a plurality of candidate embolic regions associated with the region to include in the set of candidate embolic regions. Identifying the set of embolic regions from among the set of candidate embolic regions may comprise assigning at least one candidate embolic region of the set of candidate embolic regions as being an embolic region to include in the set of embolic regions, the assigning performed at least in part by using the at least one statistical model.

Some embodiments are directed to a method, comprising: obtaining data identifying an ultrasound signal associated with a patient; identifying a set of candidate embolic regions in the data; and identifying a set of embolic regions from among the set of candidate embolic regions. Identifying the set of candidate embolic regions may comprise assigning a region in the data as being a candidate embolic region at least in part by using at least one statistical model relating at least one feature of the region to physiological information; and determining a plurality of candidate embolic regions associated with the region to include in the set of candidate embolic regions. Identifying the set of embolic regions from among the set of candidate embolic regions may comprise assigning at least one candidate embolic region of the set of candidate embolic regions as being an embolic region to include in the set of embolic regions, the assigning performed at least in part by using the at least one statistical model.

BRIEF DESCRIPTION OF DRAWINGS

Various aspects and embodiments will be described with reference to the following figures. The figures are not necessarily drawn to scale.

DETAILED DESCRIPTION

Figure 1:
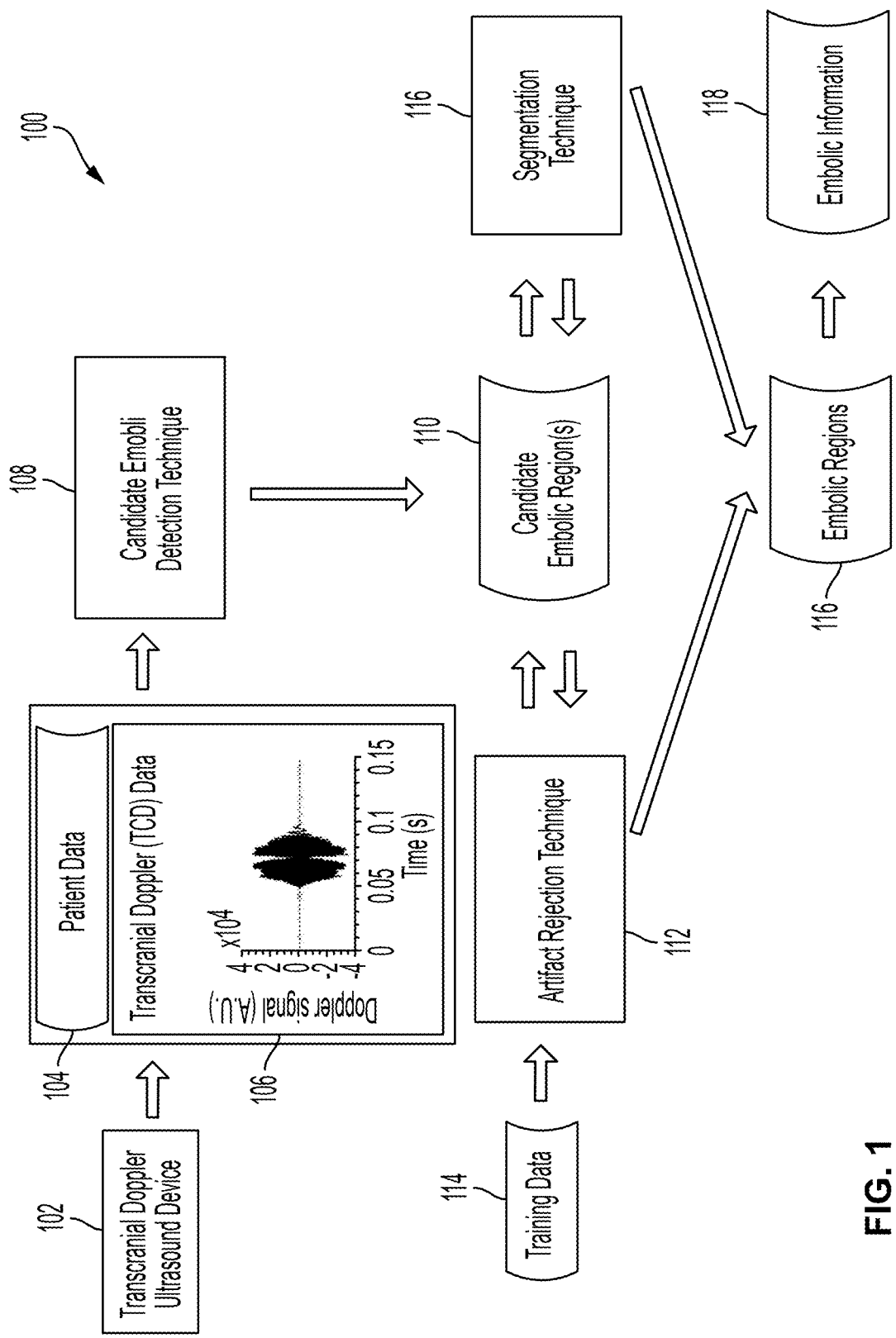
FIG. 1 is a diagram of an illustrative TCD data processing pipeline for detecting emobli, in accordance with some embodiments of the technology described herein.

Computational techniques that analyze blood flow through a patient's brain, including transcranial Doppler (TCD) ultrasound data, may be used in detecting emboli as being present in blood vessels within the patient's brain. However, the inventors have recognized that conventional techniques for detecting emboli have limitations in the accuracy of the detected embolic load (e.g., embolic counts) and the ability to analyze TCD data from single-frequency, single-depth TCD ultrasound devices. These limitations create challenges in the ability of physicians to implement TCD ultrasound in assessing the patient's risk of brain injury because of the unreliability of the detected embolic load.

For example, some conventional techniques for detecting emboli using TCD data involve computational techniques that tend to miscount the number of emboli. Artifacts in the TCD data that have similar features as embolic signals, but do not correspond to emboli, may be included in determining the embolic load, and thus lead to over counting of the number of emboli as being present in an individual. Artifacts that may be detected as being an embolus when such conventional techniques are used include artifacts arising from electromagnetic interference, patient movement, ultrasound probe movement or dislodgement, and disturbance of the patient's blood flow (e.g., when a physician administers an injection). In some instances, emboli may be misclassified as artifacts, thereby leading to under counting of the number of emboli as being present. In addition, a patient may have successive emboli occurring within a period of time, which may be referred to as an emboli cluster or emboli shower. In such instances, it can be difficult to resolve individual emboli using current conventional techniques, and under counting may occur when multiple emboli passing at the same time or at similar times across a sample volume are counted as a single embolus. As a result, these emboli detection techniques do not accurately represent the true embolic load of a patient, leading to unreliability of the embolic load detected by such techniques in assessing the patient's risk for brain injury.

Due the limited reliability of these conventional techniques, physicians often rely on their own ability to review the TCD data obtained from a patient and assess the patient's embolic load rather than use these conventional computational techniques. However, physician-based review of TCD data alone has its own limitations in accurately determining embolic load, including physician-to-physician variability, particularly in discriminating multiple emboli occurring close together and in differentiating emboli from artifacts, and can be a demanding burden on the physician's time because such review generally occurs manually and offline. In addition, there is need to have the embolic load detected in real-time to allow for ongoing monitoring of a patient's embolic condition, such as while a patient is on mechanical circulatory support (MCS). Such real-time monitoring may allow for interventions to reduce or prevent strokes and other neurological complications. If the only trustworthy analysis of TCD data is based on a physician's assessment of the TCD data, then it is challenging to implement real-time monitoring of a patient.

Accordingly, the inventors have developed new computational techniques for detecting emboli in TCD data, which allow for more accurate and reliable characterization of emboli and brain injury. These new computation techniques may involve detecting candidate embolic regions of the TCD data by using an oscillating background signal representative of blood flow and analyzing the candidate embolic regions to determine embolic regions, which can be used in determining embolic information (e.g., embolic load, embolic count). The oscillating background signal may more accurately reflect the patient's blood flow during cardiac cycles, which may allow for more accurate detection of emboli.

According to some estimates by the inventors, approximately 70% of embolic events detected using conventional techniques represent multiple embolic events. Accordingly, the inventors have developed new computational techniques for analyzing whether candidate emboli should be segmented. In particular, analyzing a candidate embolic region may involve segmenting the candidate embolic region to identify multiple embolic regions associated with the particular candidate embolic region. This computational technique may reduce or prevent under counting of emboli, particularly emboli occurring in short succession during an emboli cluster or emboli shower. The segmentation process may involve classifying a candidate embolic region as being an artifact or an embolus. The candidate embolic region classified as an embolus may be included in the identified embolic regions, and used in determining the embolic information. In some embodiments, the segmentation process and/or the classification process may be performed in iterations. For example, the artifact rejection process may be applied to a segmented candidate embolic region to assess whether it is classified as being an artifact or an embolus.

In addition, some conventional techniques for detecting emboli may involve using a TCD ultrasound device that emits two different frequencies. However, the inventors have recognized and appreciated that most of the TCD ultrasound devices prevalent in a hospital setting emit only a single frequency (e.g., 2 MHz). These new computational techniques for detecting emboli may be performed using TCD data obtained from a TCD ultrasound device configured to emit a single frequency. These techniques developed by the inventors for emboli detection may allow for TCD ultrasound to be implemented more widely in detecting emboli and assessing a patient's risk of brain injury because of the prevalent use of single frequency TCD ultrasound devices. However, it should be appreciated that the techniques described herein are not limited to using an ultrasound device operating at a specific frequency or at a single frequency. In some embodiments, data from a multi-frequency ultrasound device may be analyzed using these techniques, such as by applying the techniques to the individual frequencies that the ultrasound device emits.

Additionally, some conventional techniques for detecting emboli may involve using a TCD ultrasound device that detects at multiple depths, such as by using multi-gated techniques, to detect an emboli traveling at different depths. The new computational techniques developed by the inventors allow for emboli detection with a desired accuracy by detecting at a single depth, rather than by having to use a TCD device that detects at multiple depths.

The inventors have further recognized and appreciated that it is important to accurately detect emboli in real-time, particularly for monitoring risk of brain injury (e.g., stroke, delirium, and neurocognitive impairment), so that immediate interventions to reduce or prevent strokes can be taken. Accordingly, some embodiments of the technology described herein are directed to techniques for real-time detection of emboli as data is obtained. In these embodiments, the new computational techniques developed by the inventors may be performed on segments of the TCD data to provide real-time detection of emboli.

In addition, the inventors have further recognized and appreciated that different challenges can arise in detecting emboli for patients of differing ages. For example, children and adults have different physiological and pathological characteristics, which may cause different types of challenges in implementing the same emboli detection techniques to both children and adults. Accordingly, the new computational techniques described herein may allow for more accurate emboli detection regardless of the age of the patient in comparison to conventional techniques.

While discussion of these new computational techniques developed by the inventors is discussed largely in the context of analyzing transcranial Doppler ultrasound signals, it should be appreciated that these techniques may be applied to other types of ultrasound signals and for detecting emboli at other locations within the patient or in equipment connect to the patient (e.g., a tube connected to the patient). In some embodiments, the techniques described herein may be implemented in connection with a medical machine coupled to a patient via tubing that is transporting blood. Examples of medical machines include heart-lung bypass machines, extracorporeal membrane oxygenation (ECMO) therapy, ventricular assist devices (VAD) therapy, or any other type of machine that involves transportation of blood to or from a patient. An ultrasound sensor may be coupled to the tubing that transports blood (e.g., clamped to the tubing directly) and the techniques described herein may be used to detect emboli traveling in the tubing. In some instances, the tubing to which the ultrasound sensor is coupled to may direct blood back to the patient's body from the machine and these techniques may be applied to data obtained from the ultrasound sensor in detecting embolic information for emboli that are coming from the machine and going into the patient's body. The embolic information may include the number of emboli, the size or size distribution of the emboli, and/or the composition of the emboli.

It should also be appreciated that the techniques described herein can be used for detecting emboli injury other than stroke and risk of stroke. Examples of other types of emboli injuries that may be detected using the techniques described herein include post-surgical delirium, neurocognitive impairment following sedation, cardiac catheterization and any other procedures or conditions where embolic injury may occur.

Some embodiments described herein address all of the above-described issues that the inventors have recognized with detecting emboli. However, not every embodiment described herein addresses every one of these issues, and some embodiments may not address any of them. As such, it should be appreciated that embodiments of the technology described herein are not limited to addressing all or any of the above-discussed issues with detecting emboli.

Some embodiments involve obtaining data identifying an ultrasound signal associated with a patient and determining a background signal representative of blood flow in the patient using the data. In particular, the background signal may more accurately represent the patient's cardiac cycle in comparison to a constant value background signal since blood flow varies during the cardiac cycle, such as between the systolic and diastolic phases. To account for this varying background signal, some embodiments involve determining a background signal that oscillates over time. The background signal may be used to identify candidate embolic region(s) in the data. Embolic information (e.g., embolic load, embolic count) may be determined based on the candidate embolic region(s).

In some embodiments, determining the background signal involves determining background region(s) of the data and using the background region(s) to determine the background signal. The background region(s) may be determined by performing an initial embolic region detection process that involves identifying candidate embolic region(s) and background signal region(s) in the data and using the background signal region(s) in determining the background signal. An embolus-to-blood ratio for the data may be computed and used to determine the background region(s). According to some embodiments, the background region(s) may be determined by identifying a segment of the embolus-to-blood ratio as being below a threshold value and including a region of the data corresponding to the identified segment in the background region(s) used in determining the background signal. In some embodiments, determining the background signal involves computing a combination of multiple oscillating signals. According to some embodiments, the background signal may be modeled as a linear combination of oscillating signals (e.g., Fourier series).

Some embodiments involve updating the background signal in real-time to account for additional data. This may allow for the background signal adjustment to physiological or environmental changes over time. In such instances, different background signals (e.g., different linear combinations) may be determined for different time periods for the data and the background signal for a particular region of the data may be used in identifying the candidate embolic region(s).

Identifying the candidate embolic region(s) may involve computing an embolus-to-blood ratio for the data and comparing the embolus-to-blood ratio to the background signal.

In some embodiments, a detection threshold value may be used in identifying the candidate embolic region(s) where a segment of the embolus-to-blood ratio that is above the background signal by at least the detection threshold value is identified as being a candidate embolic region. The candidate embolic region(s) may correspond to high intensity transient signals (HITS) within the data.

Some embodiments involve analyzing the candidate embolic region(s) to identify embolic region(s) in the data, which can be used in providing embolic information (e.g., embolic load, embolic count) for the patient. Analyzing the candidate embolic region(s) may include an artifact rejection process that involves assigning one or more of the candidate embolic region(s) as being an artifact and not including the assigned candidate embolic region(s) in the identified embolic region(s). In this manner, a candidate embolic region corresponding to an artifact will be removed from being considered as an embolic region. As part of the artifact rejection process, one or more features of the data may be analyzed to classify whether a candidate embolic region is an artifact region or an embolic region. One feature is unidirectionality of the candidate embolic region because emboli generally move in the direction of blood flow. The unidirectionality may be determined based on the frequency spectrum of the TCD data (e.g., the Fourier transform of the Doppler signal). Another feature is spectral concentration of a candidate embolic region because emboli are expected to move at a finite range of velocities such that the expected spectral frequency is concentrated around a center frequency. A third feature is speed for a candidate embolic region. A fourth feature is distance traveled, based on the velocity calculated for a candidate embolic region, normalized to a sample volume. A fifth feature is temporal skewness, which corresponds to the start of a candidate embolic region to the peak of the candidate embolic region divided by the total duration of the candidate embolic region. A sixth feature is the ratio of measured duration over expected duration where the expected duration is computed based on the speed corresponding to the candidate embolic region.

In some embodiments, the artifact rejection process involves using statistical model(s) relating one or more features of a candidate embolic region to physiological information (e.g., characteristic of emboli, characteristic of artifact). The statistical model(s) may be trained using TCD data corresponding to emboli and TCD data corresponding to artifacts.

Some embodiments involve segmenting candidate embolic region(s) by identifying, for a candidate embolic region, multiple candidate embolic regions existing within the particular candidate embolic region. Segmenting a candidate embolic region may include computing, using the TCD data, velocity values for the candidate embolic region. In some embodiments, thresholding techniques may be applied to the velocity values to identify multiple segments of the candidate embolic region. For example, a watershed image segmentation algorithm may be applied to an image illustrating the velocity values to identify the multiple segments.

Some embodiments involve merging two segments of the candidate embolic region if the segments meet a set of constraints indicating that the two segments are part of the same embolic event. In particular, the set of constraints may include rules to determine if the two segments are close in speed and time, have not individually traversed a significant fraction of a sample volume, and do not lead to large traveled distances when combined. According to some embodiments, the set of constraints may include that a time between an intensity of one segment and an intensity of the other segment is below a threshold value. Another constraint may be that a difference between velocity of one segment and a velocity of the other segment as being below a threshold value. A third constraint may be that the respective distance traveled for both segments is below a threshold value. A fourth constraint may be that the displacement between the two segments is less than a threshold value.

Some embodiments involve identifying embolic regions from among candidate embolic regions by performing an iterative process of the artifact rejection process and the segmentation process. In some embodiments, the artifact rejection process may be applied to candidate embolic region(s) to remove one or more of the candidate embolic region(s) assigned as being an artifact and applying the segmentation process to the remaining candidate embolic region(s). For a candidate embolic region that is segmented into multiple candidate embolic regions, the artifact rejection process may be applied to those individual candidate embolic regions in identifying a set of embolic regions.

It should be appreciated that the various aspects and embodiments described herein be used individually, all together, or in any combination of two or more, as the technology described herein is not limited in this respect.

Figure 2:
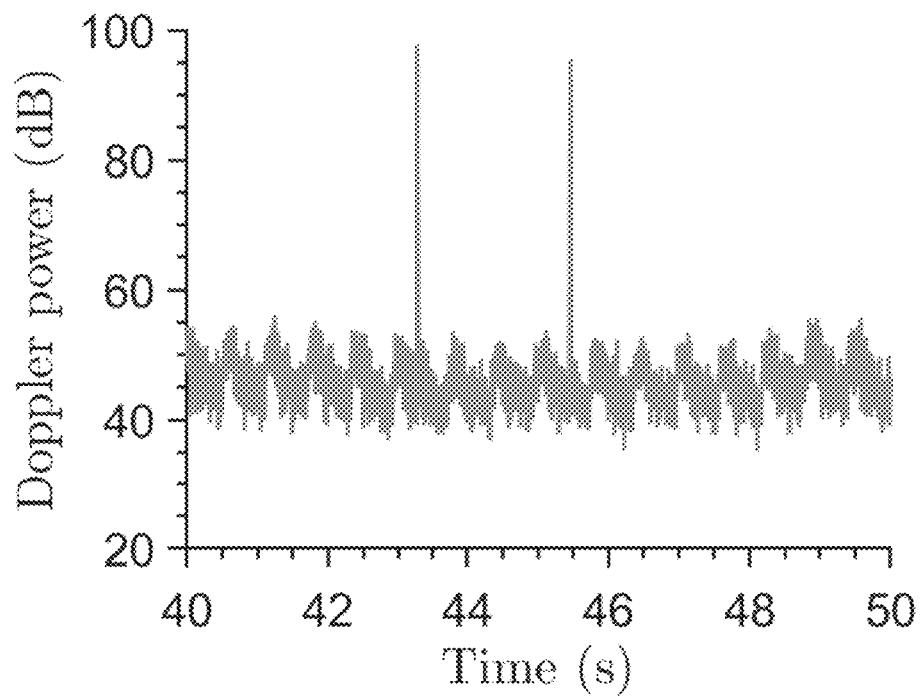
FIG. 2 is an exemplary plot of a Doppler signal versus time. The plot is an Illustration of pulsatility of Doppler power. Pusatility can vary over an order of magnitude. HITS segments are also present.

FIG. 1 is a diagram of an illustrative processing pipeline 100 for detecting emboli, which may include obtaining patient data and detecting embolic regions, in accordance with some embodiments of the technology described herein. As shown in FIG. 1, patient data 104 may be obtained and analyzed using pipeline 100. Patient data 104 may include transcranial Doppler (TCD) data 106 obtained from TCD ultrasound device 102. In some embodiments, TCD ultrasound device 102 is a TCD ultrasound device configured to emit sound waves at a single frequency (e.g., 2 MHz, 1 MHz, 3 MHz). In other embodiments, TCD ultrasound device 102 may be configured to emit multiple frequencies simultaneously. Multiple frequencies may allow for characterization of the type and/or size of emboli. TCD ultrasound device 102 may have a configuration that allows for sensing of the sound wave echoes at one or more depths of the patient's brain. It should be appreciated that the computational techniques described herein for analyzing may be implemented using TCD data 106 obtained from a single frequency and single depth TCD ultrasound device 102. TCD data 106 may include a Doppler signal obtained over a period of time. FIG. 2 is an exemplary plot of a Doppler signal versus time and illustrates pulsatility of Doppler power.

Candidate emboli detection technique 108 may be used to determine a background signal representative of blood flow in the patient and use the background signal to identify one or more candidate embolic regions 110. According to the techniques described herein, the background signal may be representative of blood flow in the patient and oscillate over time.

Determining the background signal may involve determining background region(s) of the data and using the background region(s) to determine the background signal. The background region(s) may be determined by performing an initial embolic region detection process that involves identifying candidate embolic region(s) and background signal region(s) in the data and using the background signal region(s) in determining the background signal. In particular, an embolus-to-blood ratio for the data may be computed and used to determine the background region(s). The embolus-to-blood ratio is computed by calculating a ratio of the power corresponding to high intensity transient signals (HITS) in the data to power corresponding to baseline, such as in the following equation:

$$\varepsilon_m = 10\log_{10}\left(\frac{P_m}{P_m^b}\right)$$

where $\varepsilon_m$ is the embolus-to-blood ratio, $P_m$ is the power signal, and $P_m^b$ is a baseline power level.

The initial embolic region detection process may involve identifying regions of the data that correspond to background. In some embodiments, the background region(s) may be determined by identifying a segment of the embolus-to-blood ratio as being below a threshold value and including a region of the data corresponding to the identified segment in the background region(s) used in determining the background signal.

Using the identified background region(s) of the data, candidate emboli detection technique 108 may involve determining a background signal that oscillates over time. In some embodiments, determining the background signal involves computing a combination of multiple oscillating signals. According to some embodiments, the background signal may be modeled as a linear combination of oscillating signals (e.g., Fourier series). The linear combination may include coefficients for the individual oscillating signals, and determining the background signal may include computing one or more of the coefficients.

Candidate emboli detection technique 108 may involve updating the background signal in real-time to account for additional patient data. Different background signals may be determined for different time periods for the data and the background signal for a particular region of the data may be used in identifying the candidate embolic region(s) 110. In some embodiments, updating the background signal may include updating a linear combination of oscillating signals representative of the background signal for different time periods for the data. For example, a first set of coefficients for the linear combination may be determined for a first time period and a second set of coefficients for the linear combination may be determined for a second time period.

Candidate emboli detection technique 108 involves identifying candidate embolic region(s) by using the background signal. Identifying the candidate embolic region(s) 110 may involve computing an embolus-to-blood ratio for the data and comparing the embolus-to-blood ratio to the background signal. In some embodiments, a detection threshold value may be used in identifying the candidate embolic region(s) where a segment of the embolus-to-blood ratio that is above the background signal by at least the detection threshold value is identified as being a candidate embolic region. The candidate embolic region(s) may correspond to high intensity transient signals (HITS) within the data.

Figure 3:
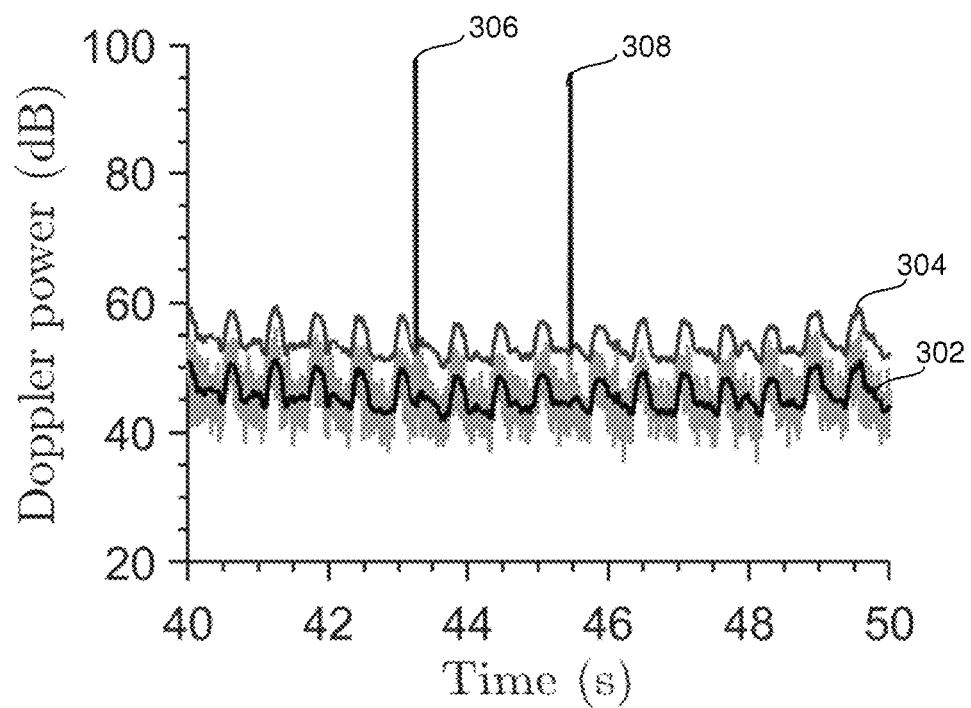
FIG. 3 is an exemplary plot of the Doppler signal shown in FIG. 2 illustrating a background signal and detected candidate embolic regions. The plot shows segemented HITS, baseline power estimate, and the detection threshold for the signal power in FIG. 2.

FIG. 3 is an exemplary plot of the Doppler signal shown in FIG. 2 illustrating background signal 302 and candidate embolic regions 306 and 308. Detection threshold 304 corresponds to a particular amount above the background signal. Regions 306 and 308 that exceed detection threshold 304 are identified as being candidate embolic regions. Regions 306 and 308 may also be referred to as high intensity transient signals (HITS). Additional discussion for determining a background signal and using the background signal to determine candidate embolic regions is described herein including in Section A.IV.A.

Figure 4:
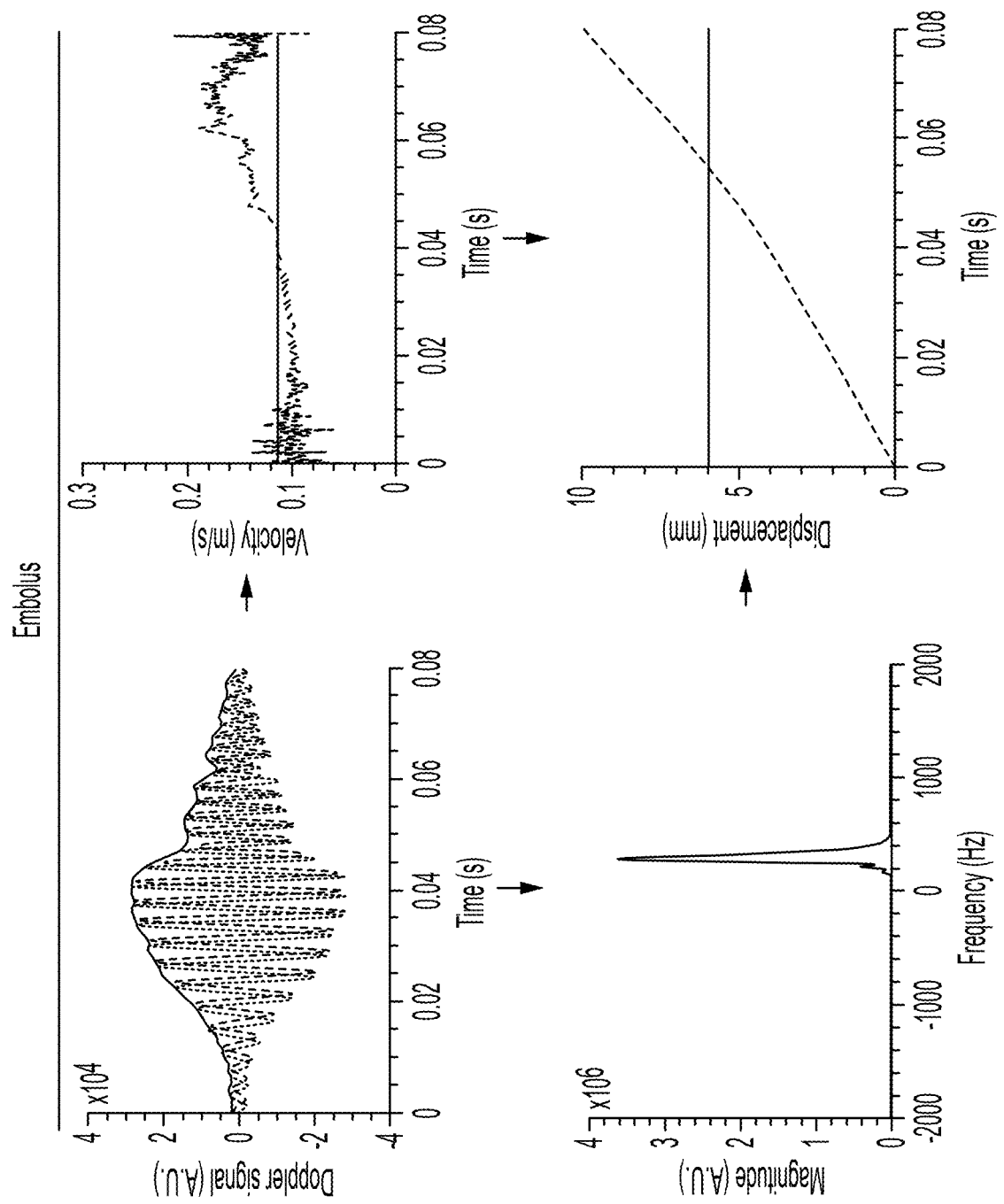
FIG. 4 are exemplary plots of Doppler signal, velocity, and displacement versus time and magnitude versus frequency for an embolus. The signal's instantaneous velocity (IV) is first determined, and its median is computed. The IV is then integrated over time to determine the HITS displacement that is subsequently normalized by the sample volume . The Fourier transforms of the Doppler signals are used to determine spectral concentration and unidirectionality. Temporal skewness is determined from the signal amplitude.
Figure 5:
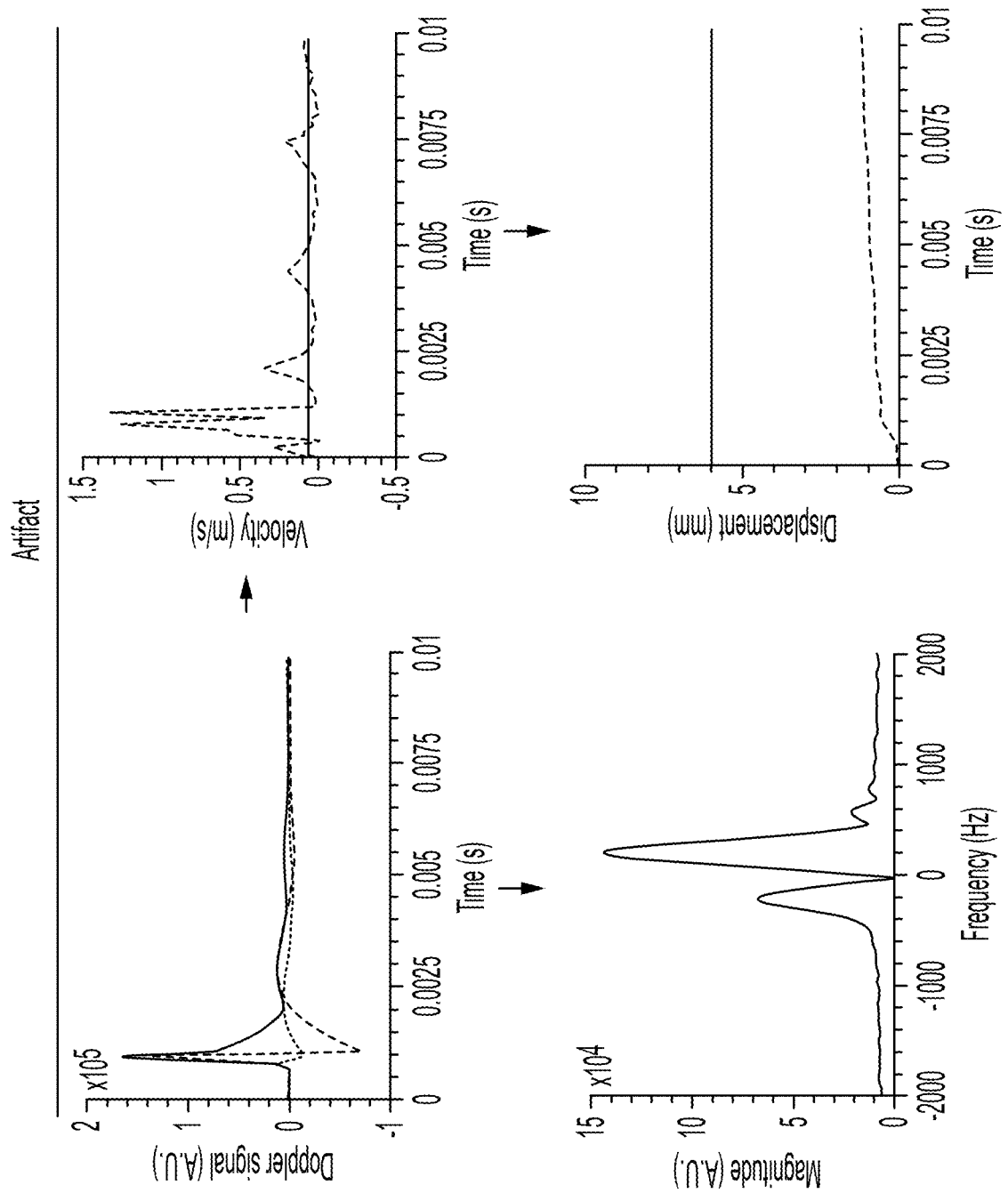
FIG. 5 are exemplary plots of Doppler signal, velocity, and displacement versus time and magnitude versus frequency for an artifact. The signal's instantaneous velocity (IV) is first determined, and its median is computed. The IV is then integrated over time to determine the HITS displacement that is subsequently normalized by the sample volume . The Fourier transforms of the Doppler signals are used to determine spectral concentration and unidirectionality. Temporal skewness is determined from the signal amplitude.

Candidate embolic region(s) 110 may be used to identify embolic region(s) 116 by applying artifact rejection technique 112 and/or segmentation technique 116 to candidate embolic region(s) 110. Artifact rejection technique 112 may involve assigning a candidate embolic region as being an embolic region and including that candidate embolic region in the set of candidate embolic regions 110 or in embolic region(s) 116. Artifact rejection technique 112 may involve assigning a candidate embolic region as being an artifact and not including the candidate embolic region in embolic region(s) 116. One or more features of the data may be analyzed to classify whether a candidate embolic region is an artifact region or an embolic region. The one or more features may include unidirectionality, spectral concentration, speed, distance traveled, temporal skewness, and the ratio of measured duration over expected duration of the candidate embolic region. FIG. 4 shows exemplary plots of Doppler signal (top left), velocity (top right), and displacement (bottom right) versus time and magnitude (bottom left) versus frequency for an embolus. In comparison, FIG. 5 shows exemplary plots of Doppler signal (top left), velocity (top right), and displacement (bottom right) versus time and magnitude (bottom left) versus frequency for an artifact. Additional discussion for how these features are calculated is described herein including in Section A.III.A.

In some embodiments, artifact rejection technique 112 may include statistical model(s) relating one or more features of a candidate embolic region to physiological information (e.g., characteristic of emboli, characteristic of artifact). The statistical model(s) may be trained using training data 114, which may include TCD data corresponding to emboli and TCD data corresponding to artifacts. In some embodiments, artifact rejection technique 112 may include using statistical model(s) that relate unidirectionality, distance traveled, and/or the ratio of measured duration over expected duration to physiological information. Additional discussion for rejecting artifacts from among candidate embolic regions to determine embolic regions is described herein including in Sections A.III.

Segmentation technique 116 may involve identifying, for a particular candidate embolic region, multiple candidate embolic regions 110 existing within the particular candidate embolic region. Segmentation technique 116 may include computing, using TCD data 106, velocity values for a candidate embolic region and using the velocity values to determine if the candidate embolic region includes more than one segment corresponding to candidate embolic regions. Segmenting technique 116 may include applying a thresholding algorithm (e.g., a watershed image segmentation algorithm) to an image of the velocity values to identify the multiple segments.

According to some embodiments, segmentation technique 116 may involve merging two segments if the segments meet a set of constraints indicating that the two segments are part of the same embolic event. One constraint may be that a time between an intensity of one segment and an intensity of the other segment is below a threshold value. Thus, some embodiments may involve merging a first segment and a second segment based on a time between a first intensity of the first segment and a second intensity of the second segment. Another constraint may be that a difference between velocity of one segment and a velocity of the other segment as being below a threshold value. Accordingly, some embodiments involve merging a first segment and a second segment based on a first velocity of the first segment and a second velocity of the second segment. A third constraint may be that the respective distance traveled for both segments is below a threshold value. In some embodiments, segmentation technique 116 may involve merging a first segment and a second segment based on a first distance traveled for the first segment and a second distance traveled for the second segment. A fourth constraint may be that the displacement between the two segments is less than a threshold value. Segmentation technique 116 may involve merging a first segment and a second segment based on a displacement between the first segment and the second segment. Additional discussion for segmenting candidate embolic regions to determine embolic regions is described herein including in Sections A.IV.B.

Figure 6:
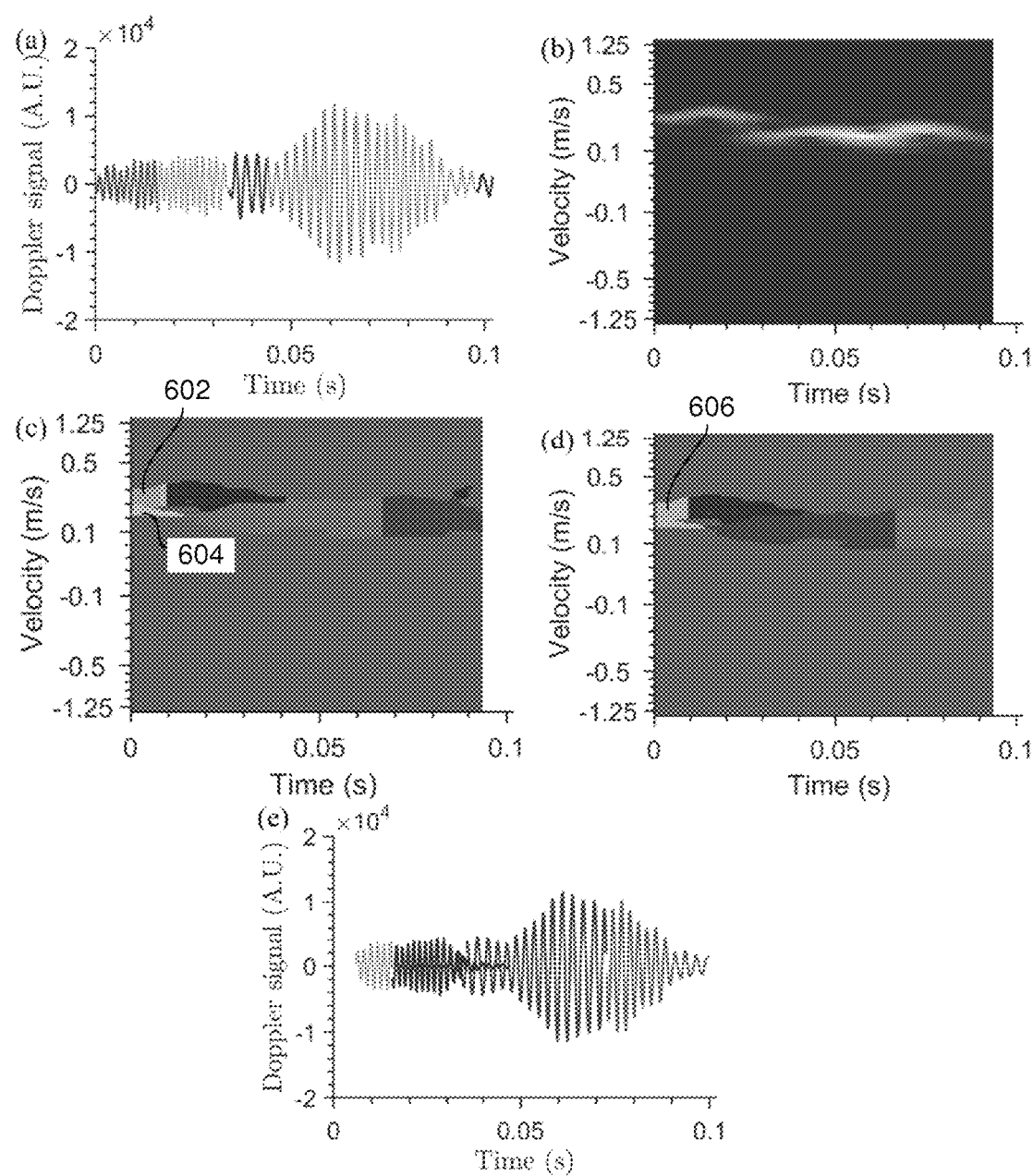
FIG. 6 are exemplary plots of Doppler signal versus time ((a) and (e)) and velocity versus time ((b), (c), and (d)) illustrating the segmentation process. The segmentation process may include: a selected embolic HITS (a) is transformed into the TF domain (b); the corresponding TF image is segmented into patches using morphological image processing (c); individual patches are merged in order to yield TF sub-domains plausibly corresponding to individual embolic segments (d); the final selected sub-domains are then transformed back to the time domain and are reclassified where the embolic segments are retained subsequently (e).

FIG. 6 are exemplary plots of Doppler signal versus time ((a) and (e)) and velocity versus time ((b), (c), and (d)) illustrating the segmentation process. FIG. 6(*a*) shows a Doppler signal corresponding to a candidate embolic region, which may be identified using candidate emboli detection technique 108. Using segmentation technique 116, velocity values corresponding to the candidate embolic region may be computed. These velocity values are illustrated in FIG. 6(*b*). A thresholding process may be applied to the velocity values to determine multiple segments for the candidate embolic region. FIG. 6(*c*) illustrates seven segments, including segments 602 and 604, which may be generated using segmentation technique 116. As discussed herein, segmentation technique 116 may involve merging two segments to determine a single candidate emboli region. FIG. 6(*d*) illustrates candidate embolic region 606 formed by merging segments 602 and 604. The resulting velocity values for the candidate embolic regions shown in FIG. 6(*d*) may be converted to the time domain, as shown in FIG. 6(*e*).

Some embodiments involve identifying embolic regions from among candidate embolic regions by performing an iterative process of using artifact rejection technique 112 and segmentation technique 116 to identify embolic regions 116. In some embodiments, artifact rejection technique 112 may be applied to candidate embolic region(s) 110 to remove one or more of candidate embolic region(s) 110 assigned as being an artifact and applying segmentation technique 116 to the remaining candidate embolic region(s) 110. Segmentation technique 116 may determine multiple segments for a candidate embolic region, and artifact rejection technique 112 may be applied to those multiple segments to determine if the individual segments correspond to an artifact or an embolus.

Figure 7:
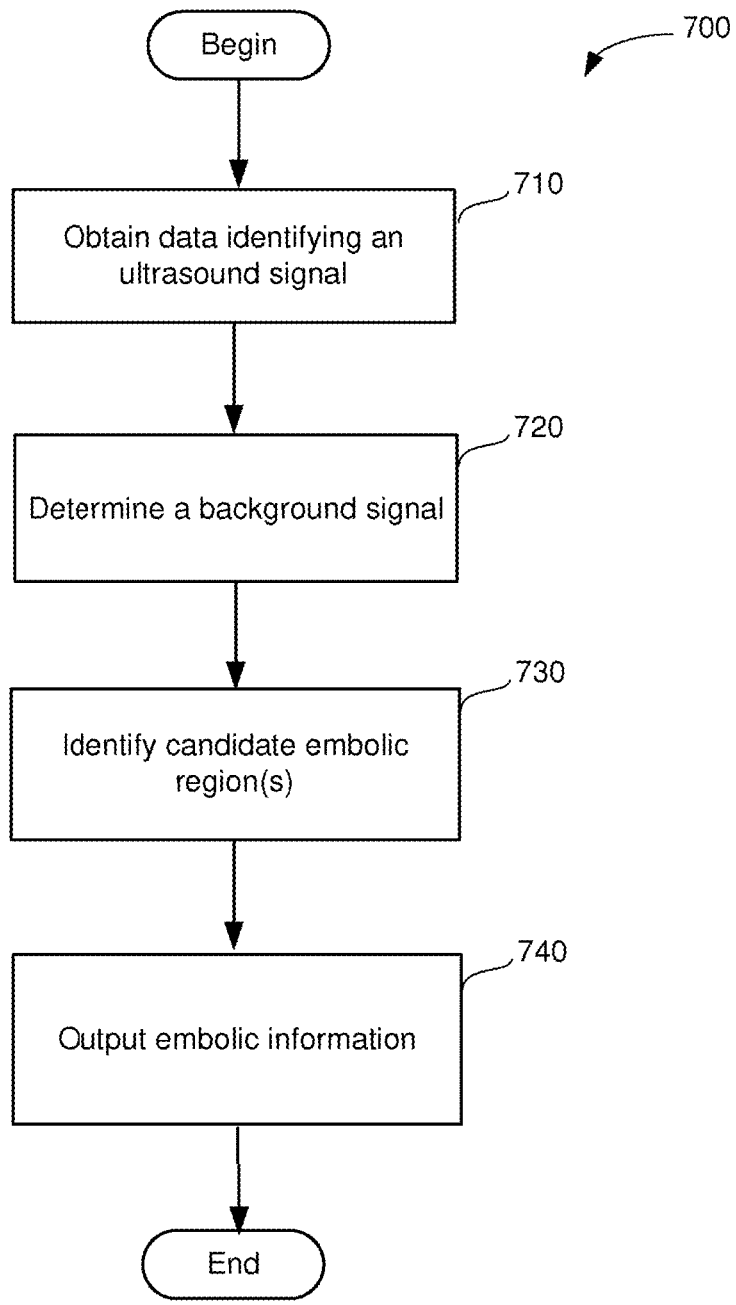
FIG. 7 is a flow chart of an illustrative process for determining embolic information, in accordance with some embodiments of the technology described herein.

FIG. 7 is a flow chart of an illustrative process 700 for determining embolic information, in accordance with some embodiments of the technology described herein. Process 700 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, candidate emboli detection technique 108 may perform some or all of process 700 to determine embolic information.

Process 700 begins at act 710, where data identifying an ultrasound signal associated with a patient is obtained. In some embodiments, the ultrasound signal may be a transcranial Doppler ultrasound signal. In some embodiments, a single frequency transcranial Doppler ultrasound device may be used in obtaining the data.

Next, process 700 proceeds to act 720, where a background signal representative of blood flow in the patient is determined, such as by using candidate emboli detection technique 108. In some embodiments, determining the background signal may involve identifying one or more background regions of the data and using the one or more background regions to determine the background signal. Identifying the one or more background regions may be performed at least in part by computing an embolus-to-blood ratio for the data and using the embolus-to-blood ratio to identify the one or more background regions. In some embodiments, identifying the one or more background regions further includes identifying a segment of the embolus-to-blood ratio as being below a threshold value and determining the one or more background regions to include a region of the data corresponding the identified segment. In some embodiments, determining the background signal is performed at least in part by computing a combination of a plurality of oscillating signals. The combination of the plurality of oscillating signals may be a linear combination of the plurality of oscillating signals. In some embodiments, determining the background signal further comprises determining, for data corresponding to a first period of time, a first background signal and determining, for data corresponding to a second period of time, a second background signal.

Next process 700 proceeds to act 730, where candidate embolic region(s) are identified using the background signal, such as by using candidate emboli detection technique 108. In some embodiments, identifying one or more candidate embolic regions is performed at least in part by computing an embolus-to-blood ratio for the data and comparing the embolus-to-blood ratio to the background signal. Identifying the one or more candidate embolic regions may further include determining a segment of the embolus-to-blood ratio as being above the background signal by at least a threshold value. In some embodiments, the one or more candidate embolic regions correspond to at least one high intensity transient signals (HITS) within the data.

Next process 700 proceeds to act 740, where an indication of embolic information based on the candidate embolic region(s) is output, such as to a user via a user interface. The embolic information may include an indication of stroke risk for the patient.

Figure 8:
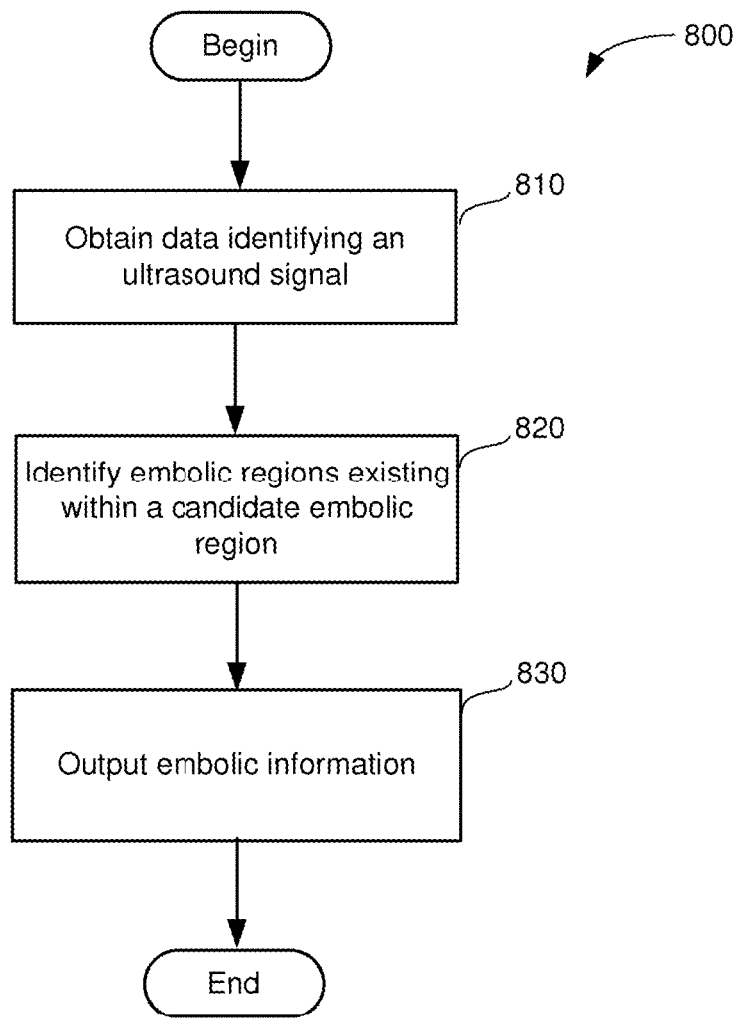
FIG. 8 is a flow chart of an illustrative process for determining embolic information, in accordance with some embodiments of the technology described herein.

FIG. 8 is a flow chart of an illustrative process 800 for determining embolic information, in accordance with some embodiments of the technology described herein. Process 800 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, candidate emboli detection technique 108 and segmentation technique 116 may perform some or all of process 800 to determine embolic information.

Process 800 begins at act 810, where data identifying an ultrasound signal associated with a patient is obtained. In some embodiments, the ultrasound signal may be a transcranial Doppler ultrasound signal. In some embodiments, a single frequency transcranial Doppler ultrasound device may be used in obtaining the data.

Next, process 800 proceeds to act 820, where multiple embolic regions are identified as existing within a candidate embolic region of the data, such as by using segmentation technique 116. Identifying the multiple embolic regions may include segmenting the candidate embolic region into a first region and a second region based on velocity values corresponding to the candidate embolic region. In some embodiments, identifying the multiple embolic regions further includes merging the first region and the second region based on a time between a first intensity of the first region and a second intensity of the second region. In some embodiments, identifying the multiple embolic regions further includes merging the first region and the second region based on a first velocity of the first region and a second velocity of the second region. In some embodiments, identifying the multiple embolic regions further includes merging the first region and the second region based on a first distance traveled for the first region and a second distance traveled for the second region. In some embodiments, identifying the multiple embolic regions further includes merging the first region and the second region based on a displacement between the first region and the second region. According to some embodiments, identifying the multiple embolic regions further includes merging the first region and the second region to generate a third region, and assigning the third region as being an embolic region to include in the multiple embolic regions.

Next process 800 proceeds to act 830, where an indication of embolic information corresponding to the embolic regions is output, such as to a user via a user interface. The embolic information may include an indication of stroke risk for the patient.

Figure 9:
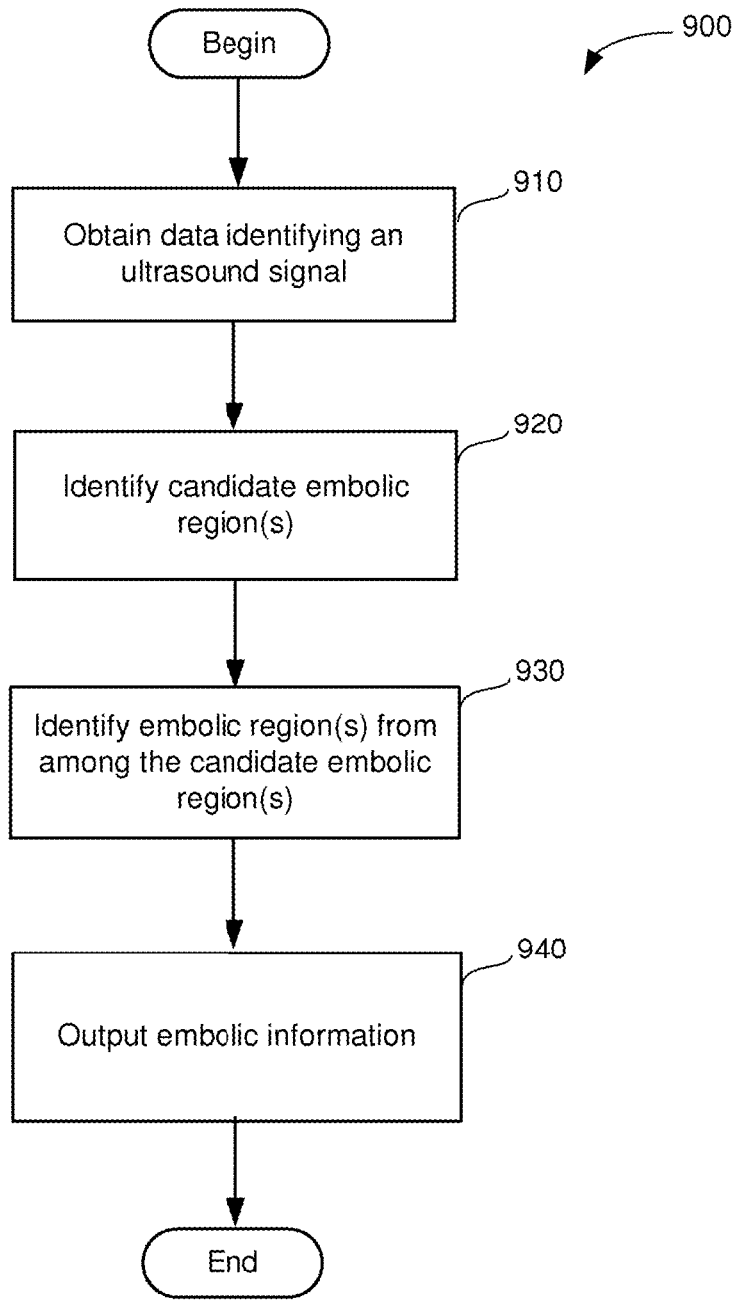
FIG. 9 is a flow chart of an illustrative process for determining embolic information, in accordance with some embodiments of the technology described herein.

FIG. 9 is a flow chart of an illustrative process 900 for determining embolic information, in accordance with some embodiments of the technology described herein. Process 900 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, candidate emboli detection technique 108, artifact rejection technique 112, and segmentation technique 116 may perform some or all of process 900 to determine embolic information.

Process 900 begins at act 910, where data identifying an ultrasound signal associated with a patient is obtained. In some embodiments, the ultrasound signal may be a transcranial Doppler ultrasound signal. In some embodiments, a single frequency transcranial Doppler ultrasound device may be used in obtaining the data.

Next, process 900 proceeds to act 920, where candidate embolic region(s) are identified in the data. Identifying the candidate embolic region(s) may include assigning a region in the data as being a candidate embolic region at least in part by using one or more statistical models relating at least one feature of the region to physiological information, for example by implementing artifact rejection technique 112. In some embodiments, identifying the candidate embolic region(s) may include determining multiple candidate embolic regions associated with the region to include in a set of candidate embolic regions, for example by using segmentation technique 116.

In some embodiments, the one or more statistical models were trained on transcranial Doppler data corresponding to emboli and transcranial Doppler data corresponding to artifacts. In some embodiments, the at least one feature includes unidirectionality of the transcranial Doppler signal. In some embodiments, the at least one feature includes displacement. In some embodiments, the at least one feature includes a ratio of a measured duration to an expected duration.

Next, process 900 proceeds to act 930, where embolic region(s) are identified from among the candidate embolic region(s). Identifying the embolic region(s) may include assigning one or more candidate embolic regions of the set of candidate embolic regions as being an embolic region to include in a set of embolic regions, for example by implementing artifact rejection technique 112. The assigning may be performed at least in part by using the at least one statistical model.

In some embodiments, identifying the embolic region(s) from among the candidate embolic region(s) may comprise assigning at least one candidate embolic region as being an artifact region. In some embodiments, identifying the embolic region(s) may comprise determining the embolic region(s) to not include the at least one candidate embolic region assigned as being an artifact region.

Next process 900 proceeds to act 940, where an indication of embolic information corresponding to the embolic regions is output, such as to a user via a user interface. The embolic information may include an indication of stroke risk for the patient.

Figure 10:
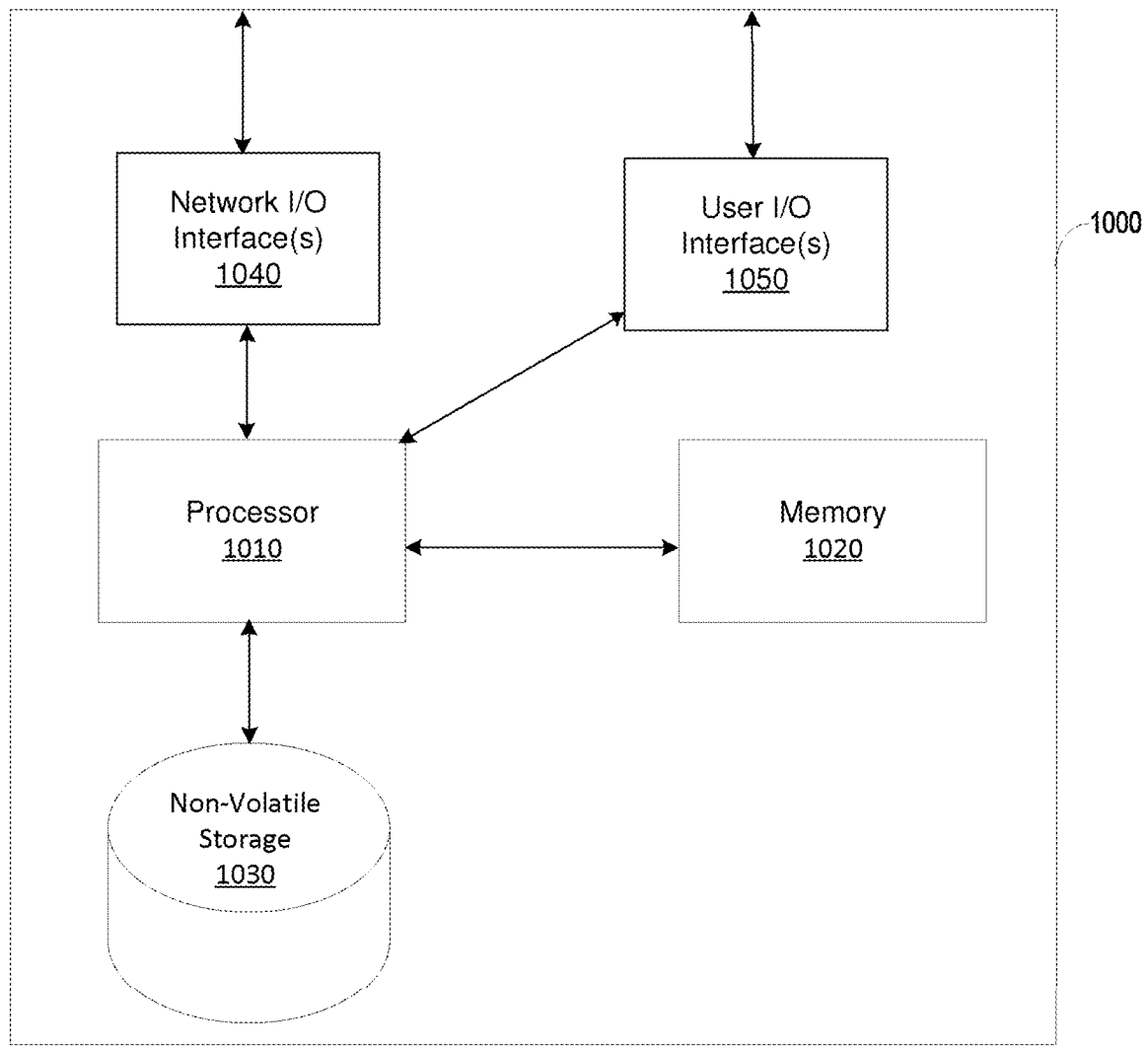
FIG. 10 is a block diagram of an illustrative computer system that may be used in implementing some embodiments of the technology described herein.

An illustrative implementation of a computer system 1000 that may be used in connection with any of the embodiments of the technology described herein is shown in FIG. 10. The computer system 1000 includes one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the technology described herein are not limited in this respect. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

Computing device 1000 may also include a network input/output (I/O) interface 1040 via which the computing device may communicate with other computing devices (e.g., over a network), and may also include one or more user I/O interfaces 1050, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Some aspects of the technology described herein may be understood further based on the non-limiting illustrative embodiments described below in Section A. Any limitations of the embodiments described below in Section A are limitations only of the embodiments described in Section A, and are not limitations of any other embodiments described herein.

Section A

Objective: To develop and validate an approach for reliable cerebral embolic load monitoring from high-intensity transient signals (HITS) recorded with single-channel transcranial Doppler (TCD) ultrasound. Methods: We propose a HITS detection and characterization method using a weighted-frequency Fourier linear combiner (WFLC) that estimates baseline Doppler signal power. An adaptive threshold power is determined by examining the Doppler signal power variance about this baseline, and HITS are extracted if their Doppler power exceeding this threshold. A logistic regression classification approach is employed to classify HITS into emboli or artifacts related to tissue or transducer motion. As signatures from multiple emboli may often be superimposed, we analyze the candidate emboli signals in the time-frequency (TF) domain to segment the signals into signatures of individual emboli. Data were collected using a commercial single-transducer TCD device with emboli detection capabilities, and twelve children were studied during extracorporeal membrane oxygenation, ventricular assist device therapy, or cardiac catheterization. A subset of HITS were reviewed, annotated, and split into training and testing sets for developing and evaluating the HITS classification algorithm. Results: The logistic regression classifier yielded 98% and 93% sensitivity for 100% specificity on training and testing data, respectively. Our method produced embolic counts that were lower (by a median of 46%) compared to commercial ultrasound system's estimates. Additionally, our method exhibited greater detection sensitivity during embolic showers compared to the commercial device. Significance: The proposed method enables, using single-channel Doppler information, sensitive detection and segmentation of embolic signatures and provides accurate embolic classification. Our approach paves the way toward more realistic embolic count monitoring.

I. Introduction

Acute neurological complications remain an important clinical problem in patients undergoing extracorporeal membrane oxygenation (ECMO) and ventricular assist device (VAD) support. One potential cause of acute brain injury in these populations may be embolism, which can be detected by transcranial doppler (TCD) ultrasonography as high intensity transient signals (HITS) within the Doppler spectrum. HITS representing cerebral emboli may be particles of thrombus, atheromatous plaque, lipid, air, or platelet aggregates that can occlude the micro- or macrovasculature, potentially causing transient ischemic attacks, stroke, or other acute neurologic injury. Knowledge about the prevalence and clinical significance of HITS in children who are treated with such life-saving mechanical circulatory assist support devices, and are at high risk of embolic events to the brain, is lacking. In a previous study on children with congenital heart disease undergoing cardiac catheterization, we conducted laborious manual analysis of HITS detected by a commercial automated algorithm, and found that quantification and discrimination of HITS into emboli and artifacts generated excessive false positive events.

Typical ultrasound-based emboli detection methods use baseband (Doppler) ultrasound data from one or two depths and up to two simultaneous insonation frequencies. Doppler signals may first be prefiltered, for example using wavelet transforms, to help isolate embolic signals from artifacts and background blood signatures. Emboli may then be detected using the embolus-to-blood ratio (EBR), defined as the ratio of backscattered power from an embolic source, normalized by the power calculated over data segments not containing any emboli. Embolic sources have a high EBR because of their size and acoustic impedance mismatch relative to surrounding blood. Robust emboli detection using EBR is a challenging task, however. A baseline power level of the Doppler signal must first be established. This baseline power estimate must vary with the cardiac cycle since the received Doppler power due to blood flow may vary by an order of magnitude between diastole and systole. Since the TCD probe may be hand-held, it is also not uncommon for signal dropouts and sharp associated changes in signal power to occur. The baseline estimate must be resilient to such sudden changes in signal quality. Ideally, baseline power computation should be done in real-time, using minimal computation and memory for implementation on embedded platforms. A detection threshold must be determined, for EBR excursions above which to be treated as candidate emboli. An artifact rejection stage must also be used since tissue or ultrasound probe motion can generate large EBRs. Such artifact rejection schemes may use HITS waveform features in conjunction with machine learning algorithms. Also, multiple emboli may flow through the ultrasound field simultaneously. For instance, some have reported that existing commercial TCD systems do not accurately estimate the number of cerebral emboli in such situations. To the best of our knowledge, the problem of separating signals from multiple simultaneous emboli using single-depth TCD systems has not been addressed in the literature.

In this paper, we seek to address this gap and propose a novel method, applicable to single-channel Doppler data, that enables real-time HITS detection and classification into likely embolic character and artifact. We model Doppler baseline power as a Fourier series, and propose using a weighted-frequency Fourier linear combiner (WFLC) to adaptively estimate the Fourier coefficients in real-time. Variance of the Doppler power about this baseline leads to an adaptive HITS detection threshold. Disabling WFLC adaptation during HITS allows us to obtain estimates of the signal background during prolonged periods of HITS showers. We then propose an algorithmic separation of signatures from individual emboli by time-frequency (TF) analysis of the selected embolic segments. Logistic regression classification is then used to reject artifacts. The method was evaluated on data from twelve pediatric patients undergoing ECMO or VAD therapy.

We first outline the data collection protocol and preprocessing steps in Section II. We then describe the design of our artifact rejection method in Section III. This method was designed using a subset of our clinical data, and was subsequently integrated into our main emboli detection approach that is described in Section IV. We present and discuss patients' embolic loads in Sections V and VI, respectively.

II. Data Collection and Preparation

A. Data Collection Protocol

The study was approved by the Boston Children's Hospital Institutional Review Board, and written informed consent was obtained for all subjects from the parents or legal guardians. Children on mechanical circulatory support (MCS) with ECMO or a VAD were eligible for study inclusion <and catheterization patients>. Subjects who lacked an acoustic window to permit TCD ultrasound examination of a middle cerebral artery were excluded after enrollment. Subjects underwent emboli monitoring of the right or left middle cerebral arteries (MCA) with a dual frequency (2+2.5 MHz), range-gated, pulsed-wave TCD system (DWL Doppler-Box™X, Compumedics Germany GmbH, Singen, Germany). The ultrasound probe was handheld, or secured in place over the right or left temporal window with a soft, elastic headband. Emboli monitoring began once an adequate Doppler signal was obtained from the M1 segment of the MCA at the level of the bifurcation of the MCA and anterior cerebral artery. Demographic and clinical data of our study population are shown in Table I.

TABLE I

Patient demographic and clinical information

| Subject | Age | Gender | Diagnosis | MCS Device | Recording Duration (min) |
|---|---|---|---|---|---|
| 1 | 3 wks | F | CHD-PA/IVS with RV-dependent coronary circulation | VAD (RA to aorta) ROTAFLOW Centrifugal Pump | 40 |
| 2 | 14 yrs | M | Acute fulminant myocarditis | ECMO (VA) (developed clot in arterial cannula) | 73 |
| 3 | 17 mo | M | Restrictive cardiomyopathy | ECMO (VA)-then VAD (LA to aorta) with CARDIOHELP then ROTAFLOW, followed by EXCOR Pediatric | 32 |
| 4 | 22 mo | M | Heart transplant with acute cellular rejection | ECMO (VA)-ECPR with cannulation via neck (RCA and RIJV) | 30 |
| 5 | 3 mo | M | CHD-HLHS s/p Stage 1 palliation | ECMO VA)-ECPR with cannulation via neck (RCA and RIJV) | 43 |
| 6 | 3 yrs | F | Congenital complete heart block with epicardial pacemaker and severe LV dysfunction | VAD-(LV to aorta) EXCOR Pediatric | 9 |
| 7 | 6 wks | M | GBS meningitis and septic shock | ECMO (VA)-cannulation via neck (RCA and RIJV) | 39 |
| 8 | 5 mo | F | CHD-complex heterotaxy with failure to wean from CPB | ECMO (VA) | 41 |
| 9 (15) | | | | Catheterization | 96 |
| 10 (16) | | | | Catheterization | 118 |
| 11 (18) | | | | Catheterization | 34 |
| 12 (21) | | | | Catheterization | 70 |
| Ensemble | | | | | 625 |

MCS; mechanical circulatory support; ECMO, extracorporeal membrane oxygenation; VA, veno-arterial; VAD, ventricular assist device; CHD, congenital heart disease; PA/IVS, pulmonary atresia/intact ventricular septum; HLHS, hypoplastic left heart syndrome; RV, right ventricle; LV, left ventricle; RA, right atrium; LA, left atrium; RCA, right carotid artery; RIJV, right internal jugular vein; ECPR, ECMO cardiopulmonary resuscitation; GBS, group B *streptococcus*; CPB, cardiopulmonary bypass; ROTAFLOW Centrifugal Pump (Maquet, Wayne, NJ); CARDIOHELP (Maquet, Wayne, NJ); EXCOR Pediatric (Berlin Heart GmbH, Berlin, Germany).

B. Data Preprocessing

The DWL Doppler-Box™X exports Doppler data from a selected depth in binary format, along with timestamps of emboli detected by the device. The device exports data from one insonation frequency (2 MHz), and the data are of the form, $r_n = r_n^i + jr_n^q$, where $r^i$ and $r^q$ are the inphase and quadrature demodulated signals for the target depth, respectively, n is a discrete sampling index, with samples recorded at the pulse repetition frequency (PRF). Multiple binary files were generated for sessions during which the acquisition parameters were modified. Parameter changes included alterations in signal gain, PRF, and target insonation depth. In such cases, we concatenated the Doppler streams from each file by rescaling the signals to a common signal gain, and by using MATLAB's resample function to resample all segments to the highest PRF used during the recording session. In accordance with prior work, we then computed the signal power, $\mathcal{P}$, in non-overlapping windows of 2 ms duration. For the $m^{th}$ non-overlapping window of length $N_p$, the power was computed as $$\mathcal{P}_m = \frac{1}{N_p} \sum_{k=1+(m-1)N_p}^{mN_p} |rk|^2$$

Using $\mathcal{P}_m$ as the basis for our subsequent work, we first designed an artifact rejection method using a subset of our data. The artifact rejection classifier was then integrated into our main emboli detection approach.

III. Design of Artifact Rejection Method

A. Semi-Automated Data Annotation

The large volume of ultrasound data collected per patient precluded fully manual HITS annotation into embolic and artifact events. Thus, we first extracted candidate HITS using an automated approach. A baseline power level, $\mathcal{P}_m^b$, was determined for the initial twenty-second period using an order statistics filter and by assuming no HITS were present in that duration.

The EBR, $\varepsilon_m$, was then computed as $$\varepsilon_m = 10\log_{10}\left(\frac{\mathcal{P}_m}{\mathcal{P}_m^b}\right)$$

Subsequent power samples were marked as HITS if their EBR exceeded a preset threshold, and the background power levels were continuously updated every 20 s using non-HITS segments.

Figure 11A:
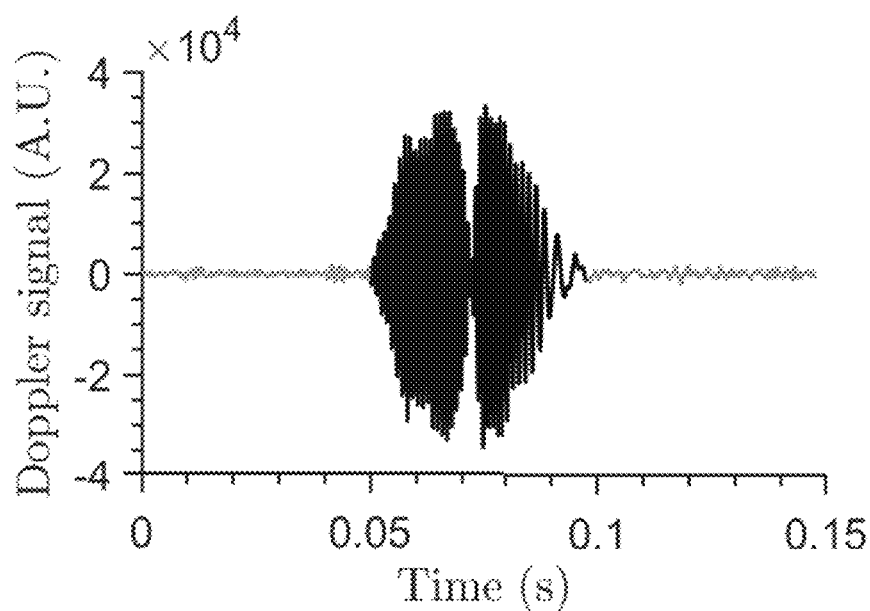
FIG. 11A is a plot of inphase signal and FIG. 11B is a plot of Doppler power, estimated background power, and HITS detection threshold. Regions above detection threshold are selected as candidate HITS. Dips in Doppler power of a candidate HITS are analyzed and sub-segments are created if the dips are below adjacent peaks by a preset threshold (sub-segments are shown with different colors).
Figure 11B:
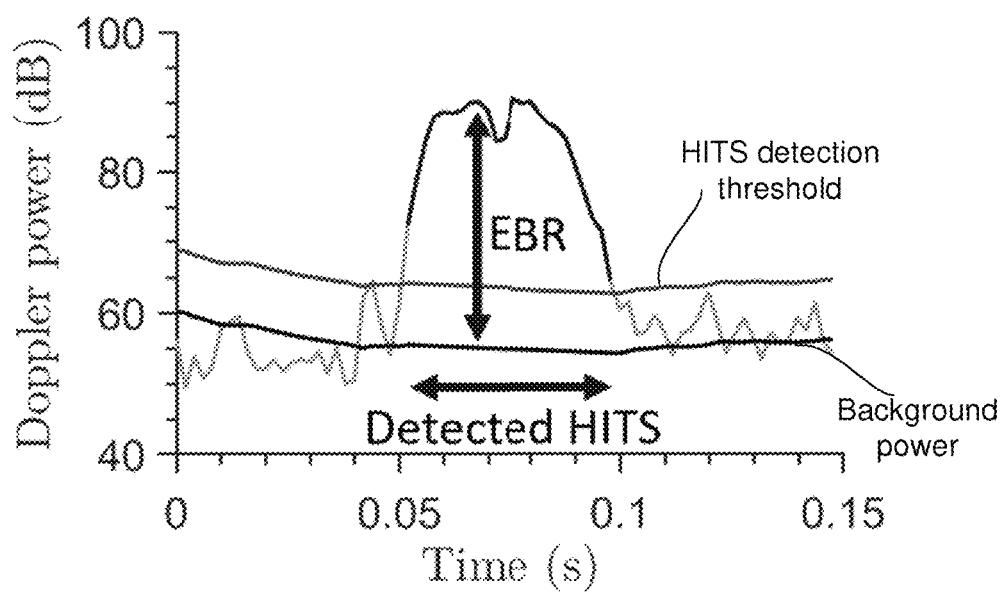

The candidate HITS so extracted can often appear temporally merged (see FIGS. 11A and 11B). Thus, we further examined the fine structure of the EBR signals for each segment. Segments lasting at least $T_{min}$=6 ms (or three 2 ms data windows) were retained, and regions longer than $T_{min}$ were split if the corresponding EBR signal locally dropped below the adjacent local EBR peaks by a preset threshold.

Two expert annotators were presented with HITS so identified from a subset of patients. Each annotator independently assessed each candidate HITS using the clinical criteria established in and indicated whether each segment was judged to be an embolic event, an artifact, or the annotator was unsure which of the two categories to assign. The majority vote was taken as the final label, with ties assigned the unsure label. A 60% cohort of data annotations from patients 2 to 7 was randomly selected and used for classifier training. The remaining annotated data were used for testing classifier performance.

B. HITS Features

Several features of the labeled HITS were computed and subsequently analyzed. The computed features include:

1) Unidirectionality: Emboli are known to move in the direction of blood flow leading to a single-sided Doppler frequency spectrum. A quantitative measure of such unidirectional flow is the ratio $\mathcal{P}_{\geq 0}/\mathcal{P}_{<0}$, where $\mathcal{P}_{\geq 0}$ and $\mathcal{P}_{<0}$ are the powers of the HITS in the positive and negative frequency bands, respectively, and blood flow is assumed to be in the positive direction. It is common, however, to simultaneously insonate two vessels with opposite flow directions, and thus a dominant blood flow direction cannot be assumed a priori. Also, the ratio can assume arbitrarily large values. Thus, we define the (nondimensional) unidirectionality, U, as $$U = \begin{cases} u/u_{max}, & u \leq u_{max} \\ 1, & u > u_{max} \end{cases}$$

$$\text{where } u = \max\left(\frac{\mathcal{P}_{\geq 0}}{\mathcal{P}_{<0}}, \frac{\mathcal{P}_{<0}}{\mathcal{P}_{\geq 0}}\right)$$

We evaluated subsequent performance for $u_{max}$=100, and computed $\mathcal{P}_{\geq 0}$ and $\mathcal{P}_{<0}$ by summing the squared magnitude values of the Blackman-windowed discrete Fourier transform (DFT), $F(\omega)$, computed over the duration of each candidate HITS (see FIGS. 4 and 5).

2) Spectral concentration: We expected emboli to travel at a finite range of velocities, leading to frequency spectra concentrated around a center frequency. We computed a measure of such spectral concentration as $$\max_\omega \left(\frac{|F(\omega)|}{\sum_\omega |F(\omega)|}\right)$$

with values close to unity indicating a high degree of spectral concentration, and with values close to zero indicating a broad frequency spectrum.

3) Speed: In contrast to emboli, artifacts have been reported to have bidirectional frequency spectra. Thus, we expected artifacts to have average Doppler speeds close to zero. We thus computed the instantaneous signal frequency, $IF_n$, by numerically differentiating the unwrapped instantaneous phase, $\arg\{r[n]\}$, of the Doppler signal such that $$IF_n \approx PRF \times \frac{\arg\{r[n]\} - \arg\{r[n-1]\}}{2\pi}$$

According to the Doppler equation, the instantaneous velocity, $IV_n$, is then $$IV_n = \frac{c}{2f_0} IF_n$$

where c=1540 m/s is the speed of sound propagation in the medium, and $f_0$=2 MHz is the transmitting frequency. Without loss of generality and for convenience, we assume here that the insonation direction is parallel to the flow direction. We then define the HITS speed for the $i^{th}$ HITS, $$s_i = \left|\underset{n}{\text{median}}(IV_n)\right|$$

4) Normalized distance: Emboli are expected to traverse a significant fraction of the target sample volume, SV. (This term is a misnomer since it is the axial length of the insonated region and not a volume, but we retain its use since the term is widely accepted). Thus, we integrate $IV_n$ over time, and normalize the absolute value of the resulting displacement by the sample-volume. In our implementation we use trapezoidal integration to compute the HITS displacement before normalizing the absolute value of the result by the sample volume.

5) Temporal skewness: We noted that artifacts tend to have a skewed temporal envelope. We therefore defined skewness as the time from the start to the peak of the envelope divided by the total HITS duration.

6) Measured/expected duration: In our visual review of sample data, we found artifacts to generally have a short duration compared to embolic signatures that are expected to have durations corresponding to their speed and sample volume. Thus the ratio of measured and expected durations can provide a means of separating artifacts from embolic events. We computed the expected duration as $\hat{t}_i$=SV/$s_i$.

C. Classifier Design

We employed logistic regression in our artifact rejection classifier. Emboli were assigned the value of 1 and artifacts the value −1. Classifiers were trained on emboli and artifacts; HITS classified as unsure were excluded from our analysis. For the $i^{th}$ HITS, the classification function is of the form $$\hat{y}_i = \begin{cases} 1, & \{1 + \exp(-h^\top g_i)\}^{-1} \geq \eta \\ -1, & \text{else} \end{cases}$$

where $\hat{y}_i$ is the algorithm-assigned label, $g_i=[1, g_{i,1}, \ldots, g_{i,J}]^T$ is the vector of J features augmented by a bias term, and $h=[h_0, h_1, \ldots, h_J]^T$ is the vector of model parameters. These parameters were obtained by minimizing the $l_2$-regularized logistic loss function $$\mathcal{L}(h) = \sum_{i=1}^{I} \ln\{1 + \exp(-y_i h^\top g_i)\} + \lambda\|h\|^2$$

where $y_i$ is the training label assigned to the $i^{th}$ HITS, I is the number of training samples, and the regularization parameter $\lambda$ was empirically set to 1. The classification threshold, $\eta$, was varied to obtain different sensitivities and specificities.

We analyzed feature statistics and trained logistic regression classifiers on individual features to gauge their artifact-rejection performance. Features were first converted to Z-scores by subtracting the respective feature mean, and dividing by the feature standard deviation in the training data. We then selected the three top performing features in this univariate analysis, and trained two classifiers—one for high classification sensitivity, and the other for high classification specificity. We employed these two classifiers in the main emboli detection scheme that is presented in the subsequent section.

IV. Embolus Detection Method

Our emboli detection approach comprises two stages. First, HITS are segmented using the EBR. Such HITS may comprise multiple embolic signatures. Thus, each detected HITS is decomposed into finer parts that are individually classified as emboli or artifacts.

A. EBR HITS Segmentation

Figure 12:
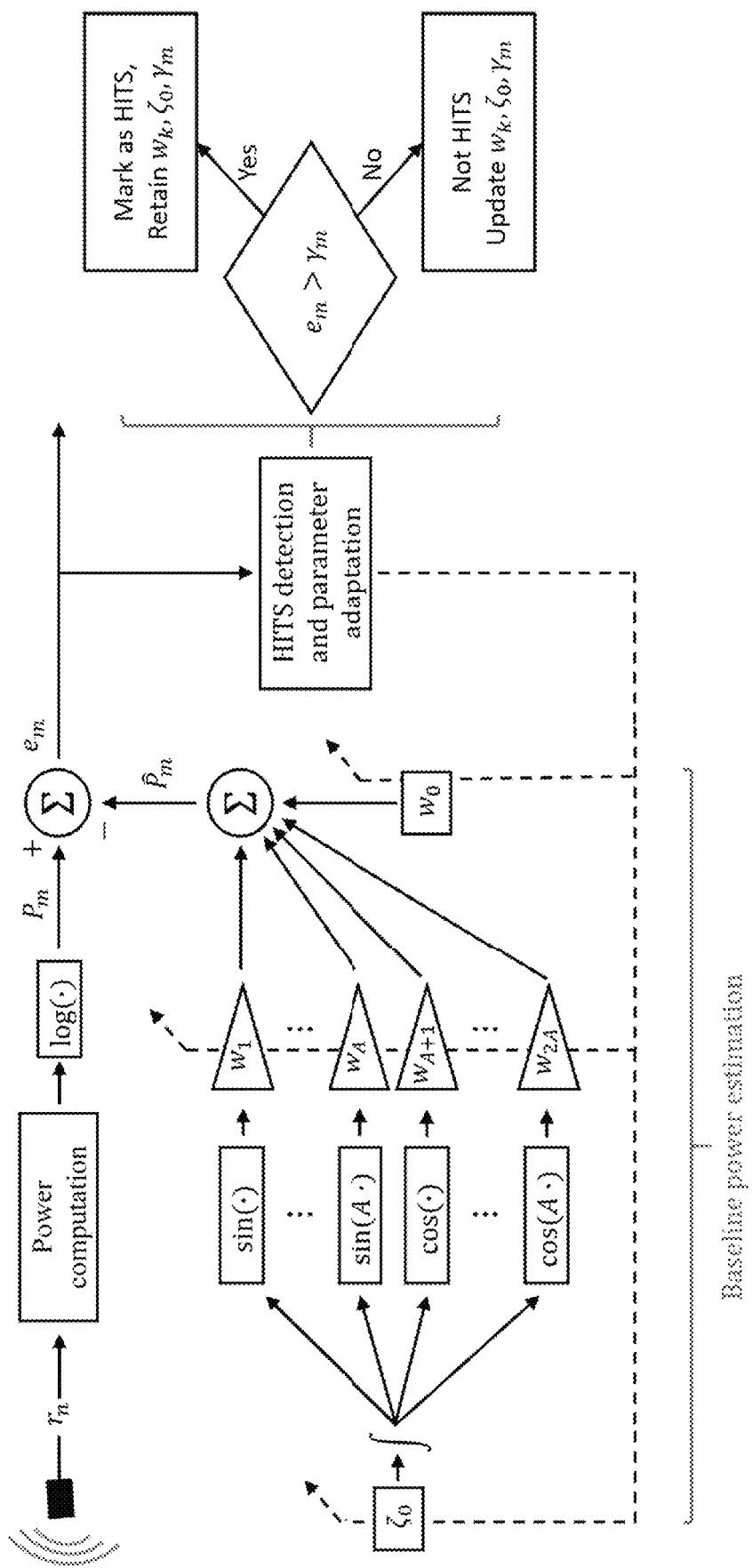
FIG. 12 is a schematic of exemplary adaptive WFLC filtering architecture. Doppler power is computed and is log-transformed. The difference of the computed and the predicted value, $\hat{P}_m$, is then used to adapt the Fourier coefficients for modeling the baseline signal. A HITS is determined if the prediction error exceeds an adaptive threshold, $\gamma_m$, in which case the Fourier coefficients are not adapted in order to retain the baseline estimate. Here, $\zeta_0$ and $\{w_i\}_{i=0}^{2A}$ are the harmonic frequency and Fourier coefficients, respectively. Dashed lines indicate adaptive steps of the WFLC architecture.

The Doppler signal power often exhibits pulsatility due to cardiac flow as shown in FIG. 2. Here we propose an adaptive baseline power estimation approach using a modified WFLC. The WFLC method was originally developed for canceling physiological tremor in robotic surgery applications. The method estimates the underlying periodic signal by modeling it as a Fourier series, and estimates both Fourier series coefficients and the harmonic frequency in an adaptive manner. We apply the WFLC method to the logarithm of the baseline power, where the logarithm is necessary for stability of parameter adaptation since the measured Doppler power can vary by orders of magnitude within a cardiac cycle. The resulting algorithm architecture is illustrated in FIG. 12.

The original WFLC method was designed to continually update its parameters. In our approach, we update the parameters only during baseline flow conditions and forgo updating when a candidate HITS is detected. We compute for each window, the difference, $e_m$, between the log-transformed power estimate, $P_m$, from a predicted log-transformed background power, $\hat{P}_m$, for that window. A HITS is detected if $e_m > \gamma_m$, where $\gamma_m$ is an adaptive threshold. The WFLC parameters and $\gamma_m$ are retained, i.e. not updated, if a HITS is detected, and are updated otherwise.

Given initial estimates for the filter weights, $w_1$ and $w_{0,1}$, and the fundamental harmonic, $\zeta_{0,1}$, a prediction at a later sample is computed as $$\hat{P}_m = w_m^T x_m + w_{0,m}$$

where $w_m = [w_{1,m}, \ldots, w_{2A,m}]^T$ are the estimated Fourier coefficients, $w_{0,m}$ is the estimated DC bias, $x_m = [x_{1,m}, \ldots, x_{2A,m}]^T$, and A is a preset number of harmonics to be estimated, where, $$x_{a,m} = \begin{cases} \sin\left(a\sum_{l=1}^{m} \zeta_{0,l}\right), & 1 \leq a \leq A \\ \cos\left((a-A)\sum_{l=1}^{m} \zeta_{0,l}\right), & A+1 \leq a \leq 2A \end{cases}$$

To update the parameters from one window to the next, we define the prediction error $$e_m \equiv \begin{cases} P_m - \hat{P}_m, & P_m - \hat{P}_m \leq \gamma_m \\ 0, & P_m - \hat{P}_m > \gamma_m \end{cases}$$

where the latter condition occurs during a HITS. Setting the associated error term to zero prevents parameter adaptation to the embolic or artifact signal properties. The WFLC parameters are then updated by performing a gradient-descent step in which $$w_{m+1} = w_m + \mu x_m e_m$$

$$w_{0,m+1} = w_{0,m+1} + \mu_0 e_m$$

$$\zeta_{0,m+1} = \zeta_{0,m} + \mu_\zeta e_m \sum_{a=1}^{A} a(w_{a,m} x_{A+a,m} - w_{A+a,m} x_{a,m})$$

where $\mu$, $\mu_0$, and $\mu_\zeta$ are preset adaptation thresholds. To initialize the computation, we provide estimates of the fundamental frequency (heart rate), and the corresponding Fourier series coefficients by computing the DFT of the first 10 seconds of $P_m$ and by analyzing the dominant frequencies, amplitudes, and phases.

To determine the detection threshold, we examine the standard deviation of prediction errors. In our method, the detection threshold is set to $$\gamma_m = \alpha \times \widehat{SD}(e_m)$$

where $\alpha$ is a tunable parameter, set here to 3, $\gamma_m$ is not allowed to exceed 15 dB for system stability, and $\widehat{SD}(e_m)$ is a low-pass filtered version of the standard deviation of the prediction errors, $\widehat{SD}(e_m)$, in HITS-free segments. A recursive low-pass filter was used of the form $$\widehat{SD}(e_m) = \alpha_{lp} \times \widehat{SD}(e_m - 1) + (1 - \alpha_{lp}) \times SD(e_m)$$

where $\alpha_{lp}$ was set to 0.9. The resulting baseline and threshold estimates for one data segment are shown in FIG. 3.

In our implementation, the WFLC parameters are reinitialized if a HITS segment longer than $T_{restart} = 10$ s is detected. This is to prevent changes in signal quality or probe position from being falsely detected as embolic signatures. HITS with a duration less than $T_{min} = 6$ ms are rejected as before. The resulting segments can be of arbitrary duration, that can lead to significant computation load in the subsequent TF analysis. To reduce this load, we split HITS into sub-segments of at most $T_{max}$=0.25 s. The WFLC parameters used in our analysis are summarized in TABLE II.

TABLE II

Segmentation parameters

| Parameter | Value |
|---|---|
| A | 2 |
| μ | 0.02 |
| $\mu_0$ | 0.01 |
| $\mu_\xi$ | $2 \times 10^{-5}$ rad/(dB2s) |
| α | 3 |
| $\alpha_{lp}$ | 0.9 |
| $T_{min}$ | 6 ms |
| $T_{max}$ | 0.25 s |
| $T_{restart}$ | 10 s |

B. Fine HITS Separation

The detected embolic HITS may be composed of multiple events or a combination of artifacts and emboli. To estimate the embolic load, we first break each HITS into sub-segments using the method in Section III with the dip threshold set to 1 dB, and classify each sub-segment using the high sensitivity three-feature classifier described above. Temporally adjacent embolic sub-segments are then analyzed further and possibly merged via TF processing.

To perform the TF analysis, we used a discrete-time approximation of the continuous wavelet transform. Specifically, a detected HITS is passed through a filter bank that enables real-time computation. Each filter is a Gaussian kernel modulated to a center frequency, fv. Each center frequency corresponds to a Doppler velocity, v, according to the Doppler equation $f_v=2f_0 v/c$. We denote the resulting TF decomposition as $R_{n,v}$, where $$R_{n,v} = r_n * h_{n,v}$$

Here $h_{n,v}$ is a bandpass filter of the form $$h_{n,v} = h_0 \frac{|f_v|}{\sqrt{2\pi PRF}} e^{-\left(\frac{n}{2\sigma_v PRF}\right)^2} e^{j2\pi f_v n/PRF}$$

where the kernel has a temporal spread governed by $\sigma_v$, and $h_0$ is a scaling constant. In our approach, we select the center velocities, v, in a logarithmic fashion, such that $V_{min} < |v| < V_{max}$, where $V_{min}=0.05$ m/s, $V_{max}=(0.5 \text{ PRF} \times c/(2f_0)) - V_{min}$) m/s, and 200 center velocities are used. We set $\sigma_v = SV/\beta v$, where $\beta=10$ is a scaling constant. Thus, filters for higher center velocities have narrower temporal spread, allowing finer temporal localization of embolic signals. A given TF image may then be inverted back to the time domain as $$R_n^{-1} = \sum_v R_{n,v}$$

Figure 13:
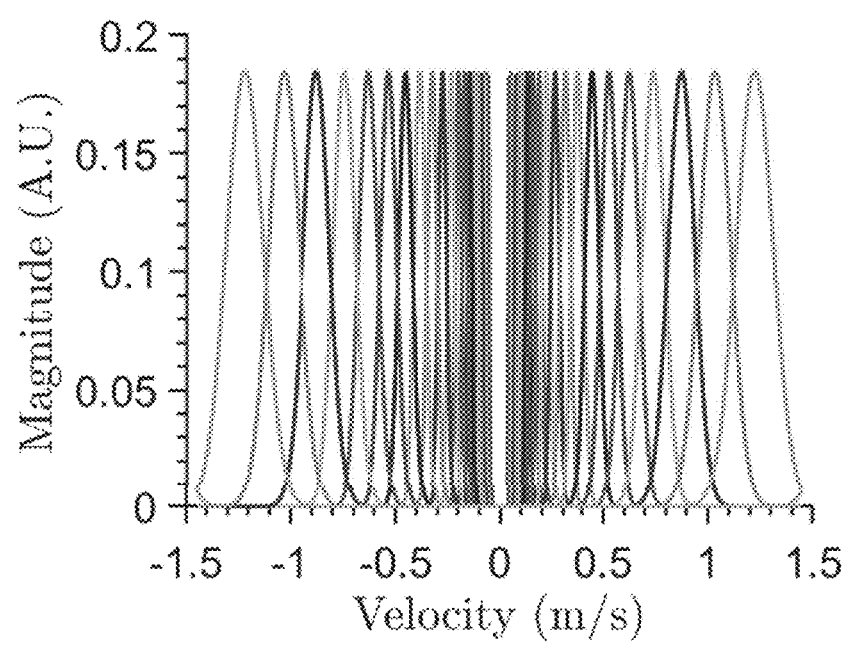
FIG. 13 is a plot of velocity (frequency) response magnitude of the filter bank. Every fifth filter is shown for ease of visualization.

The frequency response of the filter bank is shown in FIG. 13 with $h_0$=0.084 (determined empirically for invertibility with preset values of c and $f_0$).

We first segment HITS in the TF domain before conducting a linkage step to merge signatures that may correspond to the same embolus. The resulting patches are then inverted back to the time domain. We classify the time-domain patches again using our high specificity three-feature classifier to remove any artifacts. The entire process is illustrated in FIG. 6, and the individual steps are further described below.

1) TF segmentation: For each TF domain image, we generate a threshold and segment the absolute value of the TF image of the selected HITS. The threshold is generated by applying Otsu's method on log-compressed absolute values of the TF representation (MATLAB's graythresh function), and taking the anti-log of the resulting threshold. Log-compression is used since the TF pixel values can vary by several orders of magnitude, and applying the thresholding method on the raw TF images leads to unsuitable thresholds. Regions of the absolute TF representation that are higher than the threshold are segmented into patches. First, a rescaled TF image, $RS_{n,v}$ is generated according to $$RS_{n,v} = \frac{|R_{n,v}| - R_{min}}{R_{max} - R_{min}}$$

where $R_{min}$ and $R_{max}$ are the minimum and maximum absolute values in the TF representation, respectively. Rescaling allows the application of the H-minima transform to $RS_{n,v}$ in order to suppress local minima—we used an empirically determined suppression threshold of 0.001. The Watershed image segmentation algorithm is then used on the resulting image to extract patches that are above the detection threshold.

For each patch, we compute the location of the highest intensity, ($n_{max}$, $v_{max}$), and the normalized traveled distance, ND. The latter is computed by first determining the instantaneous velocity $\widetilde{IV}_n$ for each sample, n, and subsequently integrating the velocity. The absolute of the resulting displacement is normalized by the sample volume. In contrast to the computation of $\widetilde{IV}_n$ in Section III-B, the instantaneous velocity is estimated by computing a weighted average of the TF image for each n, such that $\widetilde{IV}_n = \Sigma_v |vR_{n,v}|/\Sigma_v |R_{n,v}|$. The metrics ($n_{max}$, $v_{max}$, and ND) are used subsequently to merge patches that potentially correspond to the same embolus.

2) TF merging: The segmentation process may result in disjoint patches that belong to the same embolic signal. Thus a merging step is necessary in order to avoid counting HITS spuriously. We designed a set of rules to determine if such merging is necessary. Patches are merged if they are close in speed and time, have not individually traversed a sizable fraction of the sample volume, and do not lead to large traveled distances when combined together. Specifically, two patches i and j are merged on the basis of 1) the time between their intensity maxima ($|n_{max,i} - n_{max,j}|$/PRF<T),
2) the absolute difference between their velocity maxima, ($||v_{max,i}| - |v_{max,j}||$ ≤ Δv),
3) their respective traveled distance (ND<$ND_{min}$),
4) and, the normalized displacement of the union of the patches, (ND'<$ND_{max}$).

Here, $ND_{min}$, $ND_{max}$, and Δv are predefined thresholds set to 0.85, 1.25, and 0.5 m/s, respectively, and all conditions must be met for a merger. In our approach, we consider all possible pairs of HITS until we merge a pair that fits these criteria. The process is then repeated for the new set of patches until no further matches can be made (the system reverts to the original sub-segments if the merging process does not converge within a maximum number of passes, set to 100). Finally, the merged segments are converted to the time domain. Segments are rejected if their EBR does not exceed the detection threshold for longer than $T_{min}$. The remaining segments are reclassified using our high specificity classifier, and artifacts are removed.

V. Results

A. Inter-Rater Variability

The number of HITS annotated per subject are listed in TABLE III and the inter-rater annotation agreement is summarized as a confusion matrix in TABLE IV. We quantized the inter-rater agreement using the Cohen's kappa metric, which turned out to be 51%. The annotation accuracy, or the fraction of annotations on the main diagonal of the confusion matrix, was 67%.

TABLE III

Annotation count per patient.

| Subject | Emboli | Artifacts | Unsure | Total |
|---|---|---|---|---|
| 2 | 160 | 8 | 31 | 199 (17%) |
| 3 | 0 | 36 | 23 | 59 (5%) |
| 4 | 0 | 48 | 16 | 64 (5%) |
| 5 | 0 | 50 | 0 | 50 (4%) |
| 6 | 0 | 35 | 15 | 50 (4%) |
| 7 | 0 | 126 | 9 | 135 (11%) |
| 9 | 10 | 8 | 169 | 187 (16%) |
| 11 | 72 | 23 | 108 | 203 (17%) |
| 12 | 148 | 20 | 72 | 240 (20%) |
| Ensemble | 390 (33%) | 354 (30%) | 443 (37%) | 1187 |

TABLE IV

Inter-rater confusion matrix.

| | Embolus | Artifact | Unsure | |
|---|---|---|---|---|
| Embolus | 390 (33%) | 4 (0%) | 31 (3%) | 425 (36%) |
| Artifact | 4 (0%) | 354 (30%) | 205 (17%) | 563 (47%) |
| Unsure | 52 (4%) | 97 (8%) | 50 (4%) | 199 (17%) |
| | 446 (38%) | 455 (38%) | 286 (24%) | |

B. Artifact Rejection

We took the majority vote of the annotation labels. Ties were marked as unsure entries. This resulted in 390 (33%) emboli, 354 (30%) artifacts and 443 (37%) unsure entries. HITS labeled as unsure were excluded, and 60% of data annotations from patients 2 to 7 were randomly selected and used for classifier training. Annotations from patients 9, 11, and 12, and the remaining 40% annotations from patients 2 to 7 were used for classifier testing (TABLE V).

TABLE V

Training and testing data counts.

| | Embolus | Artifact |
|---|---|---|
| Training | 96 | 182 |
| Testing | 294 | 172 |

Figure 14:
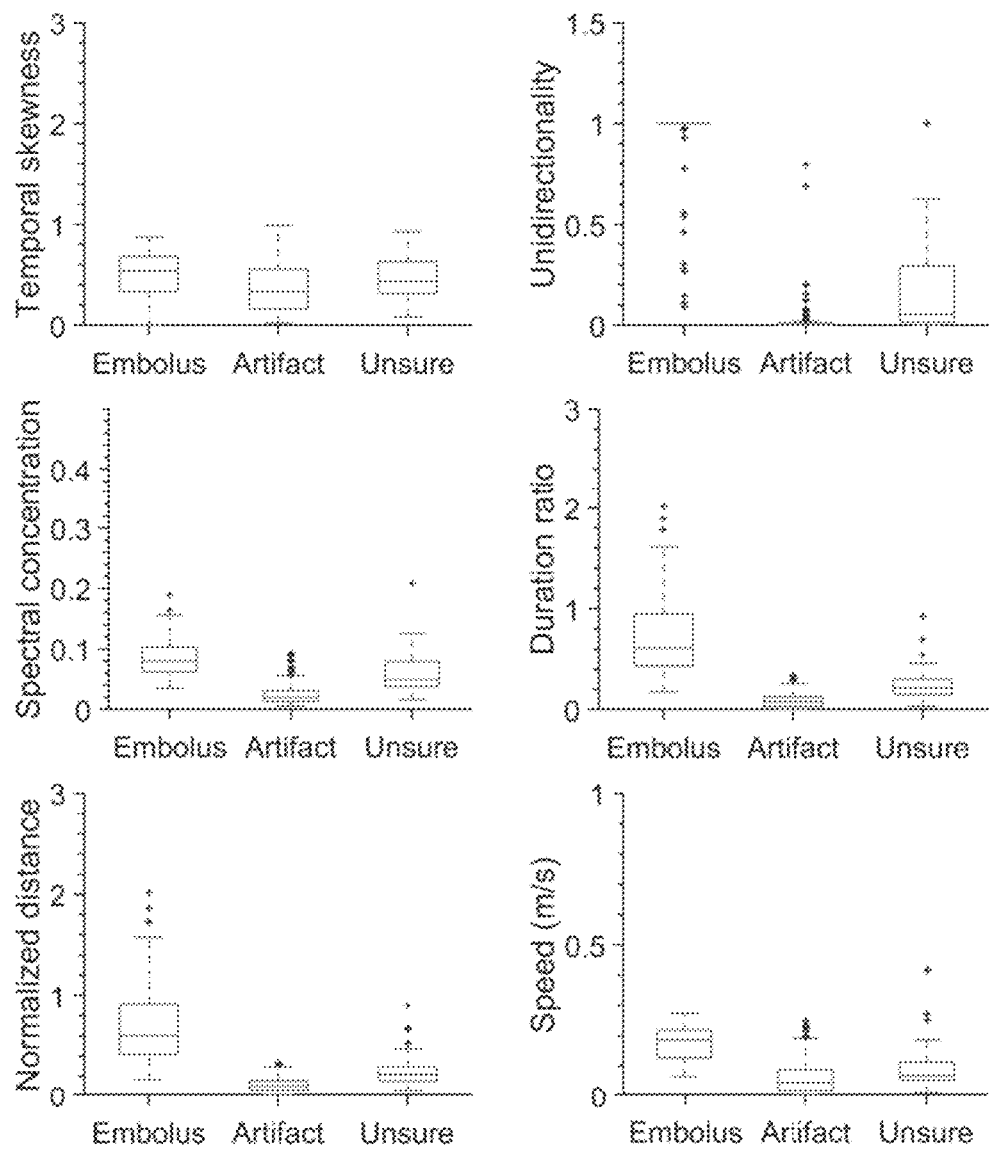
FIG. 14 shows box plots of computed features for the training data (unidirectionality computed with $u_{max}=1000$ for ease of visualization).
Figure 15:
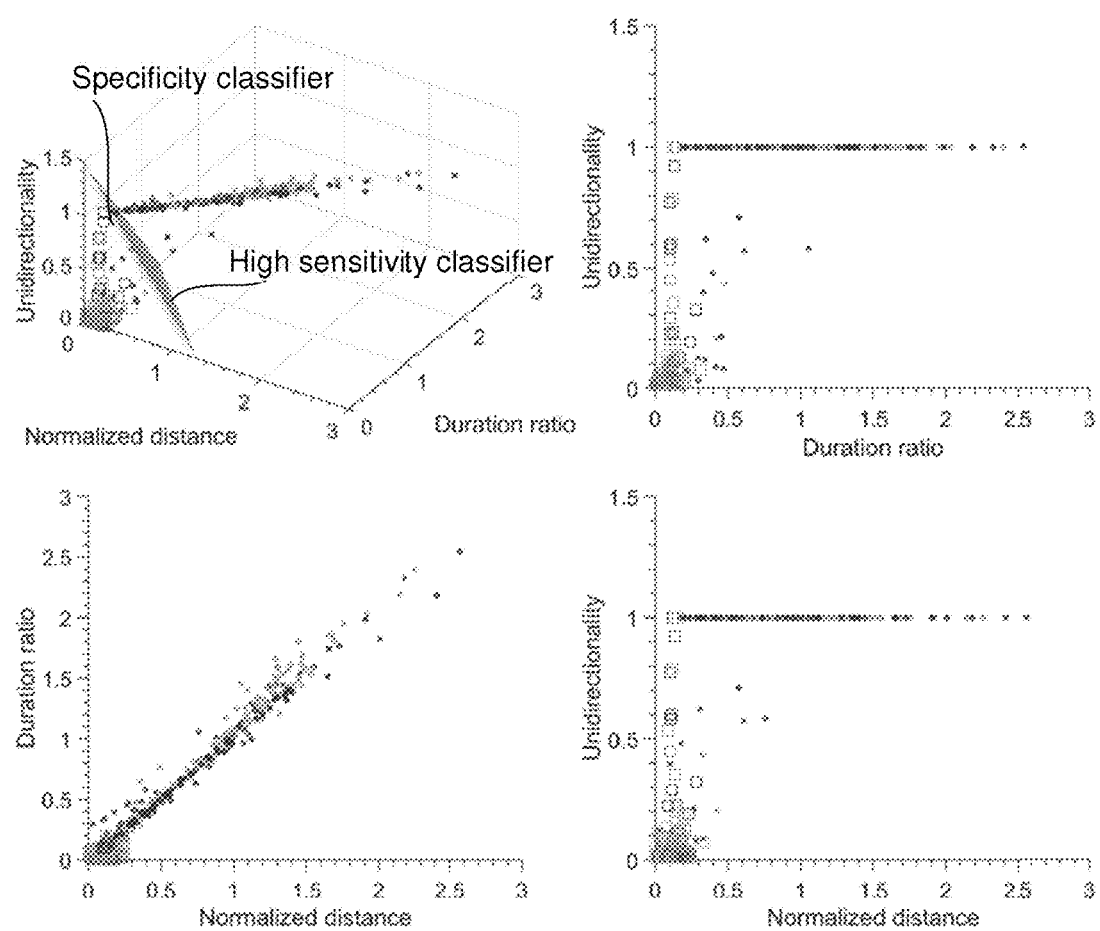
FIG. 15 shows scatter plots and 2D projections for three features of emboli (circles) and artifacts (squares) for testing data. Colors correspond to individual subjects. Artifact rejection decision boundaries for the high sensitivity and specificity classifiers are shown.

Box-plots of training data features are shown in FIG. 14. Single feature classification performance for a specificity ≥90% is summarized in TABLE VI. We then selected the three best features (normalized distance, duration ratio, and unidirectionality), and trained a logistic regression classifier on them. A scatter plot of the three features is shown in FIG. 15, where it may be seen that the duration ratio and normalized displacement features show strong collinearity for emboli. This collinearity worsens for artifacts. The performance of the three-feature classifier for a false positive rate of zero (high specificity), and true positive rate of unity (high sensitivity), respectively, is summarized in TABLE VII. The corresponding logistic regression classification weights are listed in TABLE VIII.

TABLE VI

Single-feature classifier performance: (Sensitivity, Specificity).

| | Training | Testing |
|---|---|---|
| Normalized distance | 95%, 99% | 88%, 99% |
| Duration ratio | 92%, 99% | 89%, 100% |
| Unidirectionality | 100%, 96% | 95%, 97% |
| Spectral concentration | 35%, 99% | 16%, 99% |
| Speed (m/s) | 9%, 99% | 50%, 100% |
| Temporal skewness | 15%, 91% | 4%, 93% |

TABLE VII

Performance of three-feature classifiers. 95% confidence intervals are also listed.

| | Training | | Testing | |
|---|---|---|---|---|
| | Sensitivity | Specificity | Sensitivity | Specificity |
| High specificity | 98% [95%, 100%] | 100% [100%, 100%] | 93% [90%, 96%] | 100% [100%, 100%] |
| High sensitivity | 100% [100%, 100%] | 98% [96%, 100%] | 96% [94%, 98%] | 99% [98%, 100%] |

TABLE VIII

Classifier weights.

| Feature | Weight |
|---|---|
| Normalized distance | 1.78 |
| Duration ratio | 1.81 |
| Unidirectionality | 1.84 |
| Bias | −0.91 |

C. Patient Embolic Loads

Figure 16:
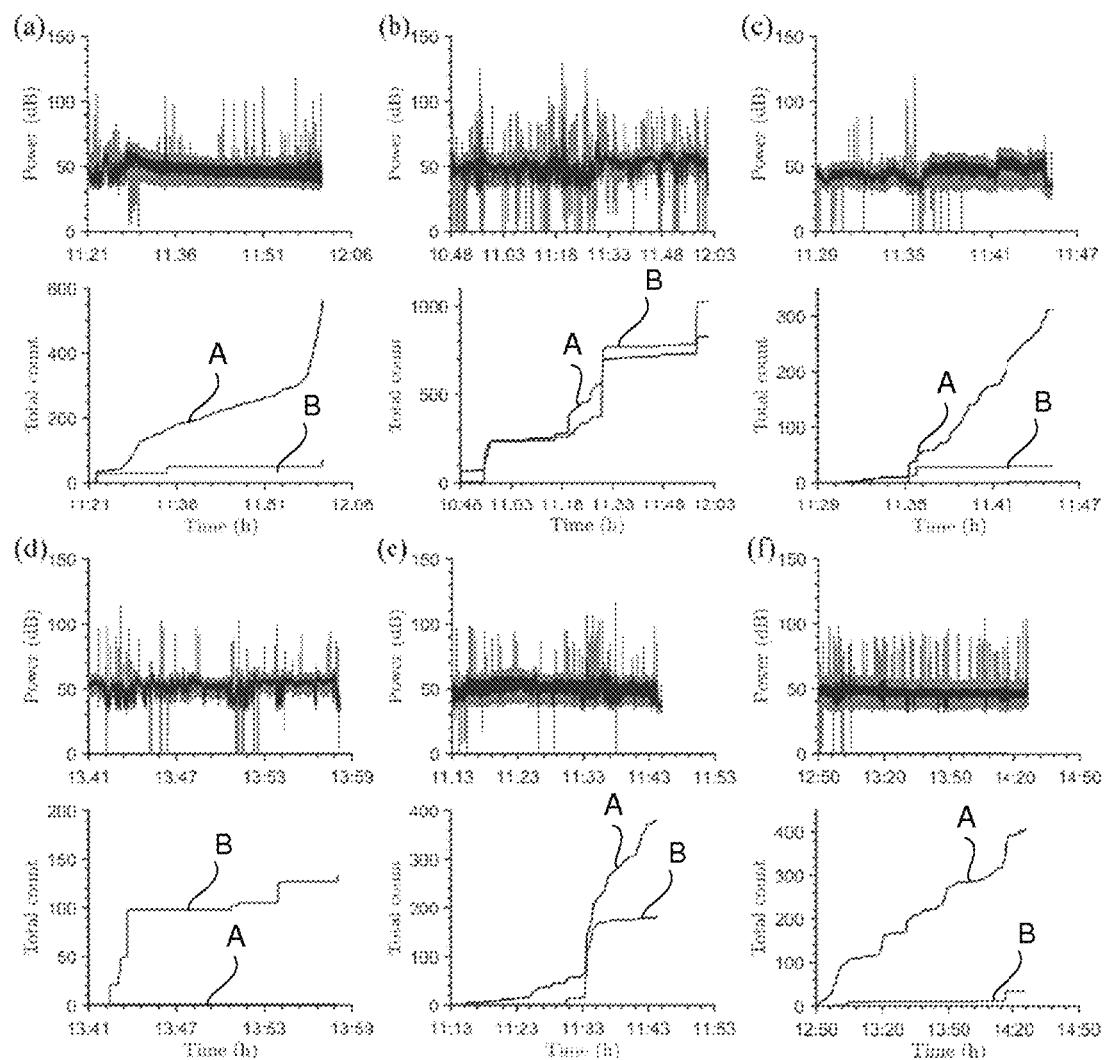
FIG. 16 shows cumulatic embolic counts for recording sessions from six patients by the DWL (labeled 'A') and a method according to the techniques described herein (labeled 'B'). The Doppler power and the estimated baseline are shown for each recording.

We applied the final emboli detection algorithm to the entire patient recordings. Cumulative embolic counts for five recordings are shown in FIG. 16, and the embolic loads are summarized in TABLE IX. The table also lists embolic counts, as classified by the high-specificity classifier, produced by only using WFLC-derived HITS, and by subdividing the former into sub-segments in the time domain using dips in EBR (denoted time domain (TD) segmentation). Relative to the manufacturer-provided counts, we obtained median percentage reduction of 57%, 44%, and 46% when using WFLC-derived segments, TD, and TF segmentation, respectively.

In the final stage of our TF analysis, we reject segments if their EBR does not exceed the detection threshold for more than $T_{min}$, and reclassify the remaining HITS using our high-specificity classifier. To assess the impact of these two stages, we computed the number of HITS rejected by them as a percentage of the final TF-derived embolic count (TABLE X). The EBR duration check rejects a median percentage of 23% of HITS, whereas the reclassification stage rejects a median percentage of 8% HITS, suggesting that they have a sizable impact on algorithm performance.

Figure 17:
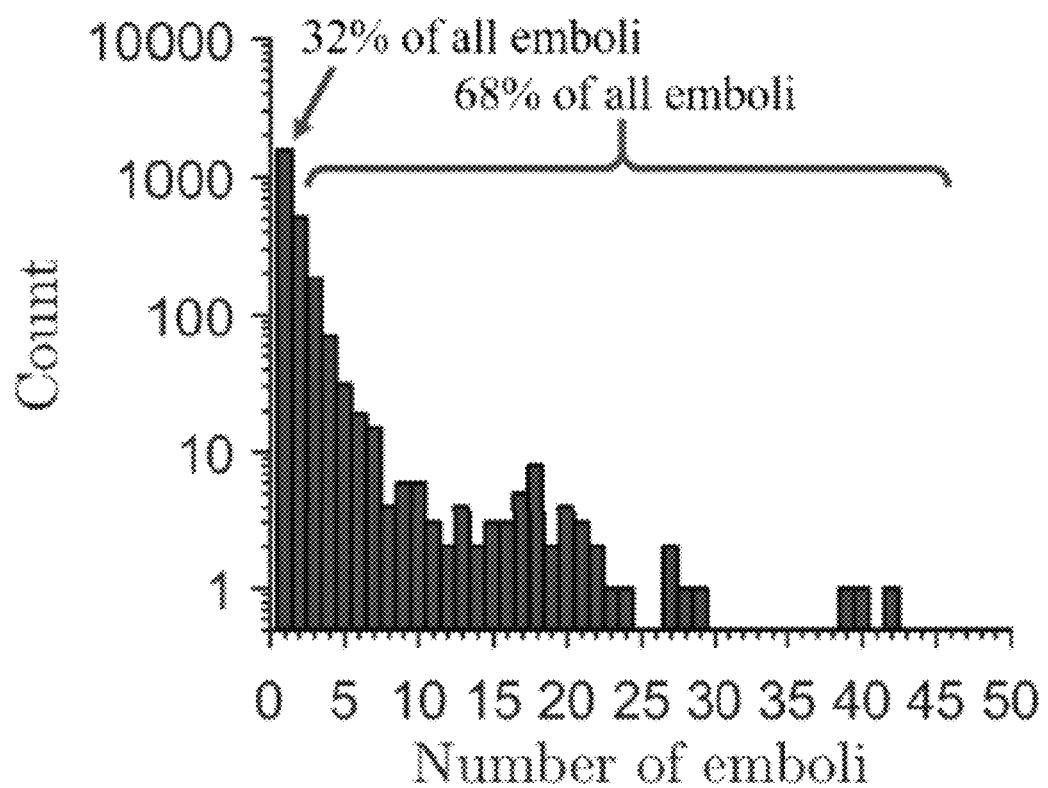
FIG. 17 is a histogram of emboli generated by TF analysis for each segment extracted by the WFLC method.

A histogram of the number of emboli generated for each WFLC-derived HITS is shown in FIG. 17, and shows that 36% of embolic HITS segmented by the WFLC method were split into two or more emboli. These sub-segments accounted for 68% of the final embolic count (i.e. 68% of the area of the histogram).

TABLE IX

Embolic loads per patient with only WFLC segmentation, with EBR-based HITS separation (TD), and with TF processing. Percentage differences relative to manufacturer-supplied embolic counts and listed in parentheses.

| Subject | DWL | Proposed | | |
| --- | --- | --- | --- | --- |
| | | WFLC | TD | TF |
| 1 | 564 | 41 (−93%) | 72 (−87%) | 70 (−88%) |
| 2 | 835 | 534 (−36%) | 1051 (26%) | 1029 (23%) |
| 3 | 608 | 144 (−76%) | 310 (−49%) | 245 (−60%) |
| 4 | 98 | 41 (−58%) | 46 (−53%) | 45 (−54%) |
| 5 | 93 | 1 (−99%) | 1 (−99%) | 1 (−99%) |
| 6 | 88 | 38 (−57%) | 50 (−43%) | 53 (−40%) |
| 7 | 43 | 61 (42%) | 146 (240%) | 208 (384%) |
| 8 | 427 | 149 (−65%) | 234 (−45%) | 208 (−51%) |
| 9 | 410 | 18 (−96%) | 34 (−92%) | 34 (−92%) |
| 10 | 554 | 498 (−10%) | 694 (25%) | 666 (20%) |
| 11 | 77 | 84 (9%) | 141 (83%) | 164 (113%) |
| 12 | 1364 | 926 (−32%) | 2036 (49%) | 2159 (58%) |
| Total (Median %) | 5164 | 2535 (−57%) | 4815 (−44%) | 4882 (−46%) |

TABLE X

Percentage of embolic counts rejected by TF-processing stages relative to final number of embolic segments.

| Subject | Duration check | Reclassification |
| --- | --- | --- |
| 1 | 19% | 26% |
| 2 | 31% | 4% |
| 3 | 27% | 13% |
| 4 | 62% | 18% |
| 5 | 0% | 0% |
| 6 | 21% | 15% |
| 7 | 26% | 13% |
| 8 | 8% | 10% |
| 9 | 59% | 6% |
| 10 | 10% | 4% |
| 11 | 24% | 2% |
| 12 | 20% | 2% |
| Median | 23% | 8% |

IV. Discussion

Several limitations of existing Doppler-based embolus detection methods have been reported in the literature. These include requiring computations that operate over large signal blocks, thereby limiting realtime operation, generation of excessive false positive events, and an inability to distinguish multiple emboli that flow through the insonation region simultaneously. We have developed a novel single-depth, single-insonation-frequency embolus detection method that attempts to address these problems. We introduced a WFLC framework to generate baseline power estimates of received Doppler data. Segments whose power exceeds the baseline by an adaptively estimated threshold were selected as candidate emboli. We integrated artifact rejection capability into our system that, using time-frequency analysis, also attempts to separate embolic signatures that flow into the ultrasound beam concurrently. When compared to the embolus detection performance of a commercially available, two-depth, dual-frequency device, our method led to a median 46% reduction in embolic counts in a pediatric patient cohort.

Computation requirements: Our system does not utilize information from future signal values, thereby allowing it to function in realtime, albeit with latency inherent in the internal computations. Preliminary HITS detection is performed with minimal delay since signal power computation introduces only a 2 ms latency (2 ms nonoverlapping data windows are used), and because the WFLC algorithm does not introduce additional delay—it was designed for zero-phase cancellation of periodic disturbances. A high-sensitivity classifier is used to reject unmistakable artifacts in order to minimize subsequent computation burden. The classification procedure itself uses three, easy-to-compute features in a simple logistic regression model. We designed our finite impulse response (FIR) filter bank such that each filter has the same group delay. Thus, these filters may be implemented as a set of parallel, causal delay lines to generate time-frequency representations of candidate HITS with a latency equal to the group delay. In our subsequent TF analysis, we employ commonly used image processing tools, optimized implementations of which are readily available for target deployment platforms.

Artifact rejection performance: Our classification efficacy is predicated on HITS training labels provided by our expert annotators who achieved an inter-rater reliability (Cohen's kappa) of 51%. Our reference annotations may thus be interpreted as reliable. Higher kappa values (72%, 79%, and 90%) have previously been reported in literature for embolus annotations by human experts. This difference is primarily because it was difficult to distinguish unequivocally in our data.

Our artifact rejection scheme uses a logistic regression classifier that allows simple interpretation of the f actors driving high classification sensitivity and specificity. Specifically, upon examining the classifier weights (TABLE VIII), it may be seen that the three features are weighted nearly equally, with slightly greater emphasis on unidirectionality. The attained high classification sensitivity and specificity is at par with that reported in prior literature. For instance, some have reported embolus classification sensitivity of 95% and a specificity of 97% on a testing dataset comprising 600 emboli and 530 artifacts.

In their approach, the authors view signals with a peak frequency below 300 Hz as artifact, and those with peak frequency above 600 Hz as emboli. For signals with peak frequencies in between, the authors base their decision on the time delay for the signal to appear in a second distal channel. Some have previously proposed using four features in a decision tree: difference in Doppler shift due to dual-frequency insonation (2 and 2.5 MHz), a measure of expected signal duration, presence in a second depth, and unidirectionality. They reported that 99% of all artifacts and emboli were classified correctly by their system in a dataset comprising 554 emboli and 800 artifacts. In our approach, we found that while the HITS speed (or equivalently, the signal frequency) is different between artifacts and emboli (FIG. 14), the attained classification accuracy in our dataset for this feature was not strong.

Our classification approach is attractive because it uses information only from one depth. During our initial experiments, we found that several emboli may flow simultaneously, making it difficult reliably match their signatures across different depths. Likewise, we only use information from one insonation frequency. The traveled distance feature has previously been shown to discriminate between gaseous and solid emboli. We found this metric to be useful in separating artifacts from emboli as well.

Embolus separation using TF analysis: Multiple emboli can often be generated simultaneously, for instance due to specific operations in cardiac surgery (including catheter manipulation and aorta cross-clamp release). Single-channel Doppler devices have been reported to be incapable of reliably detecting emboli in such circumstances. Instead, methods have been proposed that use information from multiple depths (M-mode imaging), or raw radio-frequency (RF) data. For instance, some have proposed an image processing approach using consecutive received RF ultrasound signals to improve the estimation of the number of emboli encountered in embolic showers during cardiopulmonary surgical procedures. They claim that existing TCD systems do not accurately estimate the number of cerebral emboli during such showers. Using RF data is akin to processing information from a range of depths, and allows the authors to separate signals from multiple emboli more easily, albeit at the expense of processing requirements.

To the best of our knowledge, the problem of separating signals from multiple simultaneous emboli using single-depth TCD systems has not been addressed in the literature. For instance, some extract HITS patches from Doppler TF images using a line-tracking procedure, but do not explicitly attempt to separate close HITS. Moreover, this approach uses a segmentation threshold determined via a pre-trained neural network. Other approaches extract a region of interest in HITS spectrograms by examining asymmetric (unidirectional flow) regions, while not attempting to separate individual HITS. A sizable fraction (36%) of HITS detected by the initial segmentation stage were subsequently split into two or more emboli by our TF processing stage. Emboli split in this fashion accounted for 68% of the total embolic load. To us, this indicates the potential need to incorporate such TF analysis into existing emboli detection systems.

Our TF processing approach comprises two steps. First, we use morphological processing operations coupled with a data-dependent threshold (Otsu's method) to segment HITS patches without requiring training. Second, we merge individual patches in order to retain signatures from individual emboli. We believe that extracting signatures in this fashion is important, not just to establish accurate HITS statistics, but also for subsequent characterization of embolic signal properties (for example, their material composition). At present, we employ a set of simple heuristic rules that determine how patches are merged by analyzing the net traversed distance of the patches and the difference in velocities of those patches. In doing so, we implicitly assume that the underlying emboli do not have a wide size range (by constraining normalized displacements between $ND_{min}$ and $ND_{max}$). It has been reported that in adults, particulate emboli with diameters below 100 μm are unlikely to be detected via Doppler ultrasound owing to the diameter of the middle cerebral artery (MCA). Likewise, particulate emboli with sizes above 240 μm are reported to cause stroke. None of the patients in our cohort suffered from stroke, and hence it is plausible that the particulate emboli in our data were within a narrow size range. Future work, however, can focus on assessing particle size, to further guide the TF patch merging process.

Comparison with the DWL: The DWL device exports its detected HITS with a timestep granularity of 10 ms, thereby preventing a segment-by-segment comparison between embolic counts. We observe, however, that our embolic counts exhibit greater sensitivity during embolic showers, as exhibited by larger steps in the cumulative counts in FIG. 16. At the same time, we found that in several recordings, the device's cumulative counts exhibit linear trends, indicating a constant background embolic rate. Our method does not show such linear trends, and this difference could be due to both different detection sensitivities and embolic classification steps. On the whole, our method reduced the embolic counts by a median 46% potentially suggesting that the device may be generating excessive false positive events.

Contributions: We have proposed a single-depth, single-frequency Doppler based approach to detect, classify, and separate closely opposed emboli. The initial detection is performed via a WFLC-based method. This is attractive because it enables modeling the pulsatile nature of blood flow and also computes an adaptive detection threshold in realtime using simple computations for high detection sensitivity in both systolic and diastolic segments. We integrated our simple and interpretable logistic regression based artifact-rejection scheme into a TF processing approach in order to separate HITS into individual embolic events that may overlap in both time and frequency (velocity) using a single Doppler channel. The proposed approach, when applied to data from pediatric patients, reduced the median embolic counts by more than half, thereby warranting further exploration of accuracies of commercial devices. Likewise, integrating the ability to size emboli will enable better separation of HITS that may occur simultaneously.

VII. Conclusion

Neurological complications are an important clinical problem in adult and pediatric patients. Single-channel Doppler devices, though common in clinical environments, may lead to inaccurate embolic load estimates. The proposed embolus detection approach advances the state of the art in such single-channel, single-frequency Doppler systems by introducing a novel detection algorithm, coupled with an artifact rejection stages that uses simple-to-compute features, and by analyzing the signatures in the time-frequency domain. Our method thus potentially paves the way for ubiquitous and more reliable embolic load assessment and management in hospital settings.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

The invention claimed is:

1. A system comprising:
   at least one hardware processor; and
   at least one non-transitory computer-readable storage medium storing processor-executable instructions that, when executed by the at least one hardware processor, cause the at least one hardware processor to perform:
   obtaining data from an ultrasound signal produced by ultrasound measurements performed on a patient;
   computing an embolus-to-blood ratio for the data;
   identifying at least one segment of the data as having an embolus-to-blood ratio as being below a detection threshold value, thereby determining at least one background region of the data;
   determining, from the at least one background region of the data, a background signal representative of blood flow in the patient, the background signal oscillating over time;
   identifying at least one candidate embolic region in the data using the background signal by determining at least one segment of the data as having an embolus-to-blood ratio as being above that of the background signal by at least the threshold detection value;
   analyzing the at least one candidate embolic region to generate embolic information; and
   outputting the embolic information.

2. The system of claim 1, wherein determining the background signal is performed at least in part by computing a combination of a plurality of oscillating signals.

3. The system of claim 2, wherein the combination of the plurality of oscillating signals is a linear combination of the plurality of oscillating signals.

4. The system of claim 1, wherein determining the background signal further comprises determining, for data corresponding to a first period of time, a first background signal and determining, for data corresponding to a second period of time, a second background signal.

5. The system of claim 1, wherein the at least one candidate embolic region corresponds to at least one high intensity transient signal (HITS) within the data.

6. The system of claim 1, wherein obtaining data from an ultrasound signal produced by ultrasound measurements performed on a patient further comprises obtaining data from a transcranial Doppler signal produced by transcranial Doppler measurements performed on the patient.

7. The system of claim 1, wherein the embolic information includes an indication of risk of brain injury for the patient.

8. At least one non-transitory computer-readable storage medium storing processor-executable instructions that, when executed by at least one hardware processor, cause the at least one hardware processor to perform:
  obtaining data from an ultrasound signal produced by ultrasound measurements performed on a patient;
  computing an embolus-to-blood ratio for the data;
  identifying at least one segment of the data as having an embolus-to-blood ratio as being below a detection threshold value, thereby determining at least one background region of the data;
  determining, from the at least one background region of the data, a background signal representative of blood flow in the patient, the background signal oscillating over time;
  identifying at least one candidate embolic region in the data using the background signal by determining at least one segment of the data as having an embolus-to-blood ratio as being above that of the background signal by at least the threshold detection value;
  analyzing the at least one candidate embolic region to generate embolic information; and
  outputting the embolic information.

9. A method, comprising:
  obtaining data from an ultrasound signal produced by ultrasound measurements performed on a patient;
  computing an embolus-to-blood ratio for the data;
  identifying at least one segment of the data as having an embolus-to-blood ratio as being below a detection threshold value, thereby determining at least one background region of the data;
  determining, from the at least one background region of the data, a background signal representative of blood flow in the patient, the background signal oscillating over time;
  identifying at least one candidate embolic region in the data using the background signal by determining at least one segment of the data as having an embolus-to-blood ratio as being above that of the background signal by at least the threshold detection value;
  analyzing the at least one candidate embolic region to generate embolic information; and
  outputting the embolic information.

10. The system of claim 1, wherein the ultrasound measurements are single frequency measurements.

11. The system of claim 6, wherein the transcranial Doppler measurements are single frequency measurements.

12. The system of claim 11, wherein the embolic information comprises the embolic load of the patient.

13. The system of claim 12, wherein the analyzing the at least one candidate embolic region to generate embolic information comprises identifying a plurality of embolic regions existing within a candidate embolic region of the at least one candidate embolic region in the data by segmenting the candidate embolic region into at least a first region and a second region based on velocity values corresponding to the candidate embolic region.

14. The system of claim 13, wherein identifying the plurality of embolic regions further comprises merging the first region and the second region based on a time between a first intensity of the first region and a second intensity of the second region.

15. The system of claim 13, wherein identifying the plurality of embolic regions further comprises merging the first region and the second region based on a first velocity of the first region and a second velocity of the second region.

16. The system of claim 13, wherein identifying the plurality of embolic regions further comprises merging the first region and the second region based on a first distance traveled for the first region and a second distance traveled for the second region.

17. The system of claim 13, wherein identifying the plurality of embolic regions further comprises merging the first region and the second region based on a displacement between the first region and the second region.

18. The system of claim 13, wherein identifying the plurality of embolic regions further comprises merging the first region and the second region to generate a third region, and assigning the third region as being an embolic region to include in the plurality of embolic regions.

19. The system of claim 1, wherein the embolic information comprises the embolic load of the patient.

20. The system of claim 1, wherein the analyzing the at least one candidate embolic region to generate embolic information comprises identifying a plurality of embolic regions existing within a candidate embolic region of the at least one candidate embolic region in the data by segmenting the candidate embolic region into at least a first region and a second region based on velocity values corresponding to the candidate embolic region.

* * * * *